(12) United States Patent  (10) Patent No.: US 6,704,595 B2
Bardy  (45) Date of Patent: Mar. 9, 2004

(54) AUTOMATED METHOD FOR DIAGNOSING AND MONITORING THE OUTCOMES OF ATRIAL FIBRILLATION

(75) Inventor: Gust H. Bardy, Seattle, WA (US)

(73) Assignee: Cardiac Intelligence Corporation, Seattle, WA (US)

( * ) Notice: Subject to any disclaimer, the term of this patent is extended or adjusted under 35 U.S.C. 154(b) by 197 days.

(21) Appl. No.: 09/929,229

(22) Filed: Aug. 13, 2001

(65) Prior Publication Data

US 2002/0099303 A1 Jul. 25, 2002

Related U.S. Application Data

(62) Division of application No. 09/441,613, filed on Nov. 16, 1999, now Pat. No. 6,411,840.

(51) Int. Cl.⁷ ................................. A61B 5/046
(52) U.S. Cl. ..................................... 600/518
(58) Field of Search ............... 607/4, 5, 9, 14; 600/508, 519, 513, 518; 128/920–925

(56) References Cited

U.S. PATENT DOCUMENTS

| | | |
|---|---|---|
| 4,531,527 A | 7/1985 | Reinhold, Jr. et al. |
| 4,686,999 A | 8/1987 | Snyder et al. |
| 4,809,697 A | 3/1989 | Causey, III et al. |
| 4,852,570 A | 8/1989 | Levine |
| 4,958,645 A | 9/1990 | Cadell et al. |
| 4,974,607 A | 12/1990 | Miwa |
| 4,987,897 A | 1/1991 | Funke |
| 5,040,536 A | 8/1991 | Riff |
| 5,113,859 A | 5/1992 | Funke |
| 5,113,869 A | 5/1992 | Nappholz et al. |
| 5,199,428 A | 4/1993 | Obel et al. |
| 5,331,549 A | 7/1994 | Crawford, Jr. |
| 5,336,245 A | 8/1994 | Adams et al. |
| 5,355,889 A | 10/1994 | Nevo et al. |
| 5,357,427 A | 10/1994 | Langen et al. |
| 5,390,238 A | 2/1995 | Kirk et al. |
| 5,416,695 A | 5/1995 | Stutman et al. |
| 5,421,343 A | 6/1995 | Feng |
| 5,437,278 A | 8/1995 | Wilk |
| 5,544,661 A | 8/1996 | Davis et al. |
| 5,553,609 A | 9/1996 | Chen et al. |

(List continued on next page.)

FOREIGN PATENT DOCUMENTS

| | | |
|---|---|---|
| EP | 0 34 2859 | 11/1989 |
| EP | 0 513 457 | 11/1992 |
| EP | 0 711 531 A1 | 5/1996 |
| WO | WO 97/39792 | 10/1997 |
| WO | WO 98/01742 | 2/1998 |

OTHER PUBLICATIONS

Moody GB, "Integration of Real–Time and Off–Line Clinical Data in the MIMIC Database," Computers in Cardiology 1997 vol. 24, pp. 585–588, Cambridge, MA USA.

*Primary Examiner*—George R. Evanisko
(74) *Attorney, Agent, or Firm*—Patrick J. S. Inouye

(57) ABSTRACT

An automated system and method for diagnosing and monitoring the outcomes of atrial fibrillation is described. A plurality of monitoring sets is retrieved from a database. Each of the monitoring sets include recorded measures relating to patient information recorded on a substantially continuous basis. A patient status change is determined in response to an atrial fibrillation diagnosis by comparing at least one recorded measure from each of the monitoring sets to at least one other recorded measure. Both recorded measures relate to the same type of patient information. Each patient status change is tested against an indicator threshold corresponding to the same type of patient information as the recorded measures which were compared. The indicator threshold corresponds to a quantifiable physiological measure of a pathophysiology resulting from atrial fibrillation.

62 Claims, 33 Drawing Sheets

U.S. PATENT DOCUMENTS

| | | |
|---|---|---|
| 5,576,952 A | 11/1996 | Stutman |
| 5,591,215 A | 1/1997 | Greenhut et al. |
| 5,687,734 A | 11/1997 | Dempsey et al. |
| 5,697,959 A | 12/1997 | Poore |
| 5,704,366 A | 1/1998 | Tracklind et al. |
| 5,711,297 A | 1/1998 | Iliff |
| 5,713,350 A | 2/1998 | Yokota et al. |
| 5,720,771 A | 2/1998 | Snell |
| 5,724,580 A | 3/1998 | Levin et al. |
| 5,724,983 A | 3/1998 | Selker et al. |
| 5,738,102 A | 4/1998 | Lemelson |
| 5,743,267 A | 4/1998 | Nikolic |
| 5,749,907 A | 5/1998 | Mann |
| 5,749,908 A | 5/1998 | Snell |
| 5,752,976 A | 5/1998 | Duffin et al. |
| 5,772,586 A | 6/1998 | Heinonen et al. |
| 5,772,604 A | 6/1998 | Langberg et al. |
| 5,778,882 A | 7/1998 | Raymond et al. |
| 5,785,650 A | 7/1998 | Akasaka et al. |
| 5,792,062 A | 8/1998 | Poon et al. |
| 5,855,593 A | 1/1999 | Olson et al. |
| 5,876,353 A | 3/1999 | Riff |
| 5,879,375 A | 3/1999 | Larson, Jr. et al. |
| 5,891,178 A | 4/1999 | Mann et al. |
| 5,897,493 A | 4/1999 | Brown |
| 5,911,132 A | 6/1999 | Sloane |
| 5,931,857 A | 8/1999 | Prieve et al. |
| 5,954,640 A | 9/1999 | Szabo |
| 5,957,861 A | 9/1999 | Combs et al. |
| 5,987,352 A | 11/1999 | Klein et al. |
| 6,024,699 A | 2/2000 | Surwit et al. |
| 6,047,203 A | 4/2000 | Sackner et al. |
| 6,050,940 A | 4/2000 | Braun et al. |
| 6,067,466 A | 5/2000 | Selker |
| 6,073,046 A | 6/2000 | Patel |
| 6,083,248 A | 7/2000 | Thompson |
| 6,093,146 A | 7/2000 | Filangeri |
| 6,095,985 A | 8/2000 | Raymond et al. |
| 6,102,856 A | 8/2000 | Groff et al. |
| 6,139,494 A | 10/2000 | Cairnes |
| 6,155,267 A | 12/2000 | Nelson |
| 6,168,563 B1 | 1/2001 | Brown |
| 6,171,237 B1 | 1/2001 | Avitall et al. |
| 6,171,256 B1 | 1/2001 | Joo et al. |
| 6,223,078 B1 * | 4/2001 | Marcovecchio ................ 607/5 |
| 6,246,992 B1 | 6/2001 | Brown |
| 6,287,252 B1 | 9/2001 | Lugo |
| 6,302,844 B1 | 10/2001 | Walker |
| 6,336,900 B1 | 1/2002 | Alleckson |
| 6,416,471 B1 | 7/2002 | Kumar |
| 6,454,705 B1 | 9/2002 | Cosentino et al. |
| 6,477,424 B1 | 11/2002 | Thompson et al. |

\* cited by examiner

Patient 1

| Set 0 | | | | Set n-2 | Set n-1 | Set n |
|---|---|---|---|---|---|---|
| $X_0$ | • | • | • | $X_{n-2}$ | $X_{n-1}$ | $X_n$ |
| $Y_0$ | • | • | • | $Y_{n-2}$ | $Y_{n-1}$ | $Y_n$ |
| $Z_0$ | • | • | • | $Z_{n-2}$ | $Z_{n-1}$ | $Z_n$ | time →

Patient 2

| Set 0 | | | | Set n-2 | Set n-1 | Set n |
|---|---|---|---|---|---|---|
| $X_{0'}$ | • | • | • | $X_{n-2'}$ | $X_{n-1'}$ | $X_{n'}$ |
| $Y_{0'}$ | • | • | • | $Y_{n-2'}$ | $Y_{n-1'}$ | $Y_{n'}$ |
| $Z_{0'}$ | • | • | • | $Z_{n-2'}$ | $Z_{n-1'}$ | $Z_{n'}$ | time →

Patient 3

| Set 0 | | | | Set n-2 | Set n-1 | Set n |
|---|---|---|---|---|---|---|
| $X_{0''}$ | • | • | • | $X_{n-2''}$ | $X_{n-1''}$ | $X_{n''}$ |
| $Y_{0''}$ | • | • | • | $Y_{n-2''}$ | $Y_{n-1''}$ | $Y_{n''}$ |
| $Z_{0''}$ | • | • | • | $Z_{n-2''}$ | $Z_{n-1''}$ | $Z_{n''}$ | time →

FIGURE 6

AUTOMATED METHOD FOR DIAGNOSING AND MONITORING THE OUTCOMES OF ATRIAL FIBRILLATION

This patent application is a divisional of Ser. No. 09/441,613 filed Nov. 16, 1999 U.S. Pat. No. 6,411,840, issued Jun. 25, 2002, the priority date of which is claimed and the disclosure of which is incorporated by reference.

FIELD OF THE INVENTION

The present invention relates in general to atrial fibrillation (AF) diagnosis and analysis, and, in particular, to an automated method for diagnosing and monitoring the outcomes of atrial fibrillation throughout disease onset, progression, regression and status quo.

BACKGROUND OF THE INVENTION

Atrial fibrillation is a heart rhythm abnormality that is one of the leading causes of cardiovascular disease-related morbidity in the world. Clinically, atrial fibrillation involves an abnormality of electrical impulse formation and conduction that originates in the atria, that is, the upper chambers of the heart. Atrial fibrillation can occur in patients with any type of underlying structural heart abnormality, such as coronary artery disease, valvular heart disease, congenital heart disease, and cardiomyopathies of various kinds, thereby complicating patient management and therapy. Further, atrial fibrillation can sometimes occur in patients with no known underlying structural abnormalities or in patients with lung disease or hormonal or metabolic disorders. As well, the occurrence of atrial fibrillation can exacerbate other disorders, for example, myocardial ischemia or congestive heart failure. Effective treatment must include weighing the presence of any comorbidities primary or secondary to atrial fibrillation and whether therapy should be directed against rate control or restoration of normal sinus rhythm.

Atrial fibrillation is characterized by multiple swirling wavelets of electrical current spreading across the atria in a disorganized manner. The irregularity of electrical conduction throughout the atria creates irregular impulse propagation through the atrioventricular node into the ventricle and can frequently cause a patient to notice a disturbingly erratic sensation of the heartbeat. These symptoms of an erratic heartbeat, or palpitation, can be trivial or seriously disturbing to the patient's daily functions. Occasionally, the impulse conduction is extremely rapid, leading to reduced diastolic filling of the heart chambers and reduced cardiac pumping action. Rapid heart rate, as well as poor coordination of atrial and ventricular pumping functions, not only lead to a decrease in cardiac output, but also, depending upon the nature of any underlying heart disease, can exacerbate heart failure, coronary blood flow, and pulmonary disorders. Atrial fibrillation may also occur and be totally inconsequential in its cardiovascular and cardiopulmonary consequences or its affect on the patient's quality of life. Yet, even if silent from a cardiovascular and symptom perspective, if persisting beyond a 48 hour period, atrial fibrillation can also result in blood clot formation in the atria, thereby creating the potential for thromboembolism which can lead to strokes or injuries to limbs and major organs. Thus, the outcomes or consequences of atrial fibrillation can be gross or subtle and be rapid or gradual in onset, consequently requiring a range of approaches, from observation to providing emergent interventions.

The early diagnosis, prevention and monitoring of the consequences of atrial fibrillation can be relatively difficult. First, atrial fibrillation onset runs an erratic, unpredictable course and is generally silent and undetectable to the patient. More often, atrial fibrillation either results in no symptoms at least for some period of time early in the course of onset, or in fatigue or difficulties in breathing usually in the case of those patients having comorbid conditions. Occasionally, a patient will have no complaints but will unconsciously compensate by limiting his or her daily activities. Sometimes, the consequences of atrial fibrillation are more overt. In any case, fatigue or difficulty breathing is often a consequence of atrial fibrillation complicating the pathophysiology of coexisting conditions of congestive heart failure, myocardial ischemia, and/or respiratory insufficiency, for example.

The susceptibility to suffer from atrial fibrillation depends upon the patient's age, gender, physical condition, presence or absence of heart failure, coronary artery disease, lung disease, and the incidence of other factors, such as diabetes, lung disease, high blood pressure, anemia and kidney function. No one factor is dispositive. Evaluations for atrial fibrillation and its consequences, with annual or even monthly checkups, provide, at best, a "snapshot" of patient wellness and the incremental and subtle clinicophysiological changes which portend the onset or progression of atrial fibrillation often go unnoticed, unless electrocardiographic documentation is obtained and simultaneously correlated with cardiovascular and cardiopulmonary physiological measures. Documentation of improvements following initiation of therapy can be equally elusive.

Nevertheless, taking advantage of frequently and regularly measured physiological measures, such as recorded manually by a patient, via an external monitoring or therapeutic device, or via implantable device technologies, can provide a degree of detection, treatment and prevention heretofore unknown. In addition, monitoring of the physiological consequences of the onset and offset of atrial fibrillation can provide invaluable guidance in directing when and what therapeutic intervention is most appropriate, particularly when atrial fibrillation is coupled with other comorbidities. For instance, patients already suffering from some form of treatable heart disease often receive an implantable pulse generator (IPG), cardiovascular or arrhythmia monitor, therapeutic device, or similar external wearable device, with which rhythm and structural problems of the heart can be monitored and treated. These types of devices are useful for detecting physiological changes in patient conditions through the retrieval and analysis of telemetered signals stored in an on-board, volatile memory. Typically, these devices can store more than thirty minutes of per heartbeat data recorded on a per heartbeat, binned average basis, or on a derived basis from, for example, extensive data regarding atrial or ventricular electrical activity, minute ventilation, patient activity score, cardiac output score, mixed venous oxygen score, cardiovascular pressure measures, and the like. However, the proper analysis of retrieved telemetered signals requires detailed medical subspecialty knowledge, particularly by cardiologists and cardiac electrophysiologists.

Alternatively, these telemetered signals can be remotely collected and analyzed using an automated patient care system. One such system is described in a related, commonly owned U.S. patent application, Ser. No. 09/324,894, filed Jun. 3, 1999, pending, the disclosure of which is incorporated herein by reference. A medical device adapted to be implanted in an individual patient records telemetered signals that are then retrieved on a regular, periodic basis using an interrogator or similar interfacing device. The telemetered signals are downloaded via an internetwork onto a network server on a regular, e.g., daily, basis and stored as sets of collected measures in a database along with other patient care records. The information is then analyzed in an automated fashion and feedback, which includes a patient status indicator, is provided to the patient.

While such an automated system can serve as a valuable tool in providing remote patient care, an approach to systematically correlating and analyzing the raw collected telemetered signals, as well as manually collected physiological measures, through applied cardiovascular medical knowledge to accurately diagnose the consequences of the onset of a particular medical condition, such as atrial fibrillation, is needed. One automated patient care system directed to a patient-specific monitoring function, albeit focused on ventricular rather than atrial arrhythmias, is described in U.S. Pat. No. 5,113,869 ('869) to Nappholz et al. The '869 patent discloses an implantable, programmable electrocardiography (ECG) patient monitoring device that senses and analyzes ECG signals to detect ECG and physiological signal characteristics predictive of malignant cardiac arrhythmias. The monitoring device can communicate a warning signal to an external device when arrhythmias are predicted. However, the Nappholz device is limited to detecting tachycardias. Unlike requirements for automated monitoring of the consequences of atrial fibrillation, the Nappholz device focuses on rudimentary ECG signals indicative of malignant cardiac tachycardias, an already well-established technique that can be readily used with on-board signal detection techniques. Also, the Nappholz device is patient specific only and is unable to automatically take into consideration a broader patient or peer group history for reference to detect and consider the progression or improvement of cardiovascular disease. Moreover, the Nappholz device has a limited capability to automatically self-reference multiple data points in time and cannot detect disease regression even in the individual patient. In addition, the Nappholz device must be implanted and cannot function as an external monitor. Also, the Nappholz device neither monitors nor treats the cardiovascular and cardiopulmonary consequences of atrial fibrillation.

More specifically, the diagnosis and treatment of atrial fibrillation using implantable anti-arrhythmia devices has been widely addressed in the prior art and is described, for example, in U.S. Pat. No. 5,931,857 ('857) to Prieve et al. and U.S. Pat. No. 5,855,593 ('593) to Olson et al. The '857 patent discloses an implantable device which continuously monitors for tachyarrhythmia conditions and an associated patient activator. Two sets of arrhythmia detection criteria are utilized for evaluating autonomous and patient-activated anti-arrhythmia therapy. The '593 patent discloses a device capable of arrhythmia detection and classification based on a set of prioritized rules. However, both the Prieve and Olson devices are directed to diagnosing and treating the arrhythmias in isolation without detailed consideration of coexisting conditions and the cardiovascular and cardiopulmonary consequences of those disorders.

As a result, there is a need for a systematic approach to detecting trends in regularly collected physiological data indicative of the onset, progression, regression, or status quo of atrial fibrillation diagnosed and monitored using an automated, remote patient care system, such need being particularly heightened in the presence of comorbidities, such as congestive heart failure, myocardial ischemia, respiratory insufficiency, and related disorders. The physiological data could be telemetered signals data recorded either by an external or an implantable medical device or, alternatively, individual measures collected through manual means. Preferably, such an approach would be capable of diagnosing the cardiovascular and cardiopulmonary consequences of both acute and chronic atrial fibrillation conditions, as well as the symptoms of other cardiovascular diseases. In addition, findings from individual, peer group, and general population patient care records could be integrated into continuous, on-going monitoring and analysis.

SUMMARY OF THE INVENTION

The present invention provides a system and method for diagnosing and monitoring the consequences of the onset, progression, regression, and status quo of atrial fibrillation and its related pathophysiological, especially cardiovascular and cardiopulmonary, consequences using an automated collection and analysis patient care system. Measures of patient cardiovascular information are either recorded by an external or implantable medical device, such as an IPG, cardiovascular or heart failure monitor, or therapeutic device, or manually through conventional patient-operable means. The measures are collected on a regular, periodic basis for storage in a database along with other patient care records. Derived measures are developed from the stored measures. Select stored and derived measures are analyzed and changes in patient condition are logged. The logged changes are compared to quantified indicator thresholds to detect findings of reduced exercise capacity, respiratory distress, or other symptoms, including palpitations, indicative of the principal cardiovascular pathophysiological manifestations of atrial fibrillation.

An embodiment of the present invention is an automated system and method for diagnosing and monitoring the outcomes, including cardiovascular and cardiopulmonary consequences, of atrial fibrillation. A plurality of monitoring sets is retrieved from a database. Each of the monitoring sets includes recorded measures relating to patient information recorded on a substantially continuous basis. A patient status change is determined in response to an atrial fibrillation diagnosis by comparing at least one recorded measure from each of the monitoring sets to at least one other recorded measure. Both recorded measures relate to the same type of patient information. Each patient status change is tested against an indicator threshold corresponding to the same type of patient information as the recorded measures that were compared. The indicator threshold corresponds to a quantifiable physiological measure of a pathophysiology resulting from atrial fibrillation.

A further embodiment is an automated collection and analysis patient care system and method for diagnosing and monitoring the outcomes of atrial fibrillation. A plurality of monitoring sets is retrieved from a database. Each monitoring set includes recorded measures that each relates to patient information and include either medical device measures or derived measures calculable therefrom. The medical device measures are recorded on a substantially continuous basis. A set of indicator thresholds is defined. Each indicator threshold corresponds to a quantifiable physiological measure of a pathophysiology resulting from atrial fibrillation and relates to the same type of patient information as at least one of the recorded measures. A change in patient status is determined in response to an atrial fibrillation diagnosis by comparing at least one recorded measure to at least one other recorded measure with both recorded measures relating to the same type of patient information. Each patient status change is compared to the indicator threshold corresponding to the same type of patient information as the recorded measures that were compared.

A further embodiment is an automated patient care system for diagnosing and monitoring the outcomes of atrial fibrillation and method thereof. Recorded measures organized into a monitoring set for an individual patient are stored into a database. Each recorded measure is recorded on a substantially continuous basis and relates to at least one aspect of monitoring reduced exercise capacity, respiratory distress, and palpitations/symptoms. A plurality of the monitoring sets is periodically retrieved from the database. At least one measure related to the onset, progression, regression, and status quo of atrial fibrillation and its consequences is evaluated. A patient status change is determined in response to an atrial fibrillation diagnosis by comparing at least one recorded measure from each of the monitoring sets to at least one other recorded measure with both recorded measures relating to the same type of patient information. Each patient status change is tested against an indicator threshold corresponding to the same type of patient information as the recorded measures that were compared. The indicator threshold corresponds to a quantifiable physiological measure of a pathophysiology indicative of reduced exercise capacity, respiratory distress, palpitations, syncope, near-syncope or other cardiovascular consequences of atrial fibrillation.

A further embodiment is an automated system and method for managing a pathophysiological outcome of atrial fibrillation. A plurality of monitoring sets is retrieved from a database. Each monitoring set includes recorded measures relating to patient information recorded on a substantially continuous basis. Atrial fibrillation is diagnosed. A pathophysiological outcome of atrial fibrillation is determined in response to the atrial fibrillation diagnosis. At least one recorded measure from each of the monitoring sets is compared to at least one other recorded measure with both recorded measures relating to the same type of patient information. Each recorded measure comparison is tested against an indicator threshold corresponding to the same type of patient information as the recorded measures which were compared. The indicator threshold corresponds to a quantifiable physiological measure of a pathophysiology resulting from atrial fibrillation. The atrial fibrillation outcome is managed through interventive administration of therapy contributing to normal sinus rhythm restoration and ventricular rate response control.

The present invention provides a capability to detect and track subtle trends and incremental changes in recorded patient information for diagnosing and monitoring the outcomes of atrial fibrillation. When coupled with an enrollment in a remote patient monitoring service having the capability to remotely and continuously collect and analyze external or implantable medical device measures, atrial fibrillation detection, prevention and tracking regression from therapeutic maneuvers become feasible.

Still other embodiments of the present invention will become readily apparent to those skilled in the art from the following detailed description, wherein is described embodiments of the invention by way of illustrating the best mode contemplated for carrying out the invention. As will be realized, the invention is capable of other and different embodiments and its several details are capable of modifications in various obvious respects, all without departing from the spirit and the scope of the present invention. Accordingly, the drawings and detailed description are to be regarded as illustrative in nature and not as restrictive.

BRIEF DESCRIPTION OF THE DRAWINGS

FIG. 6 is a record view showing, by way of example, a set of partial patient care records for care of patients with atrial fibrillation stored in the database of the system of FIG. 1;

DETAILED DESCRIPTION

Figure 1:
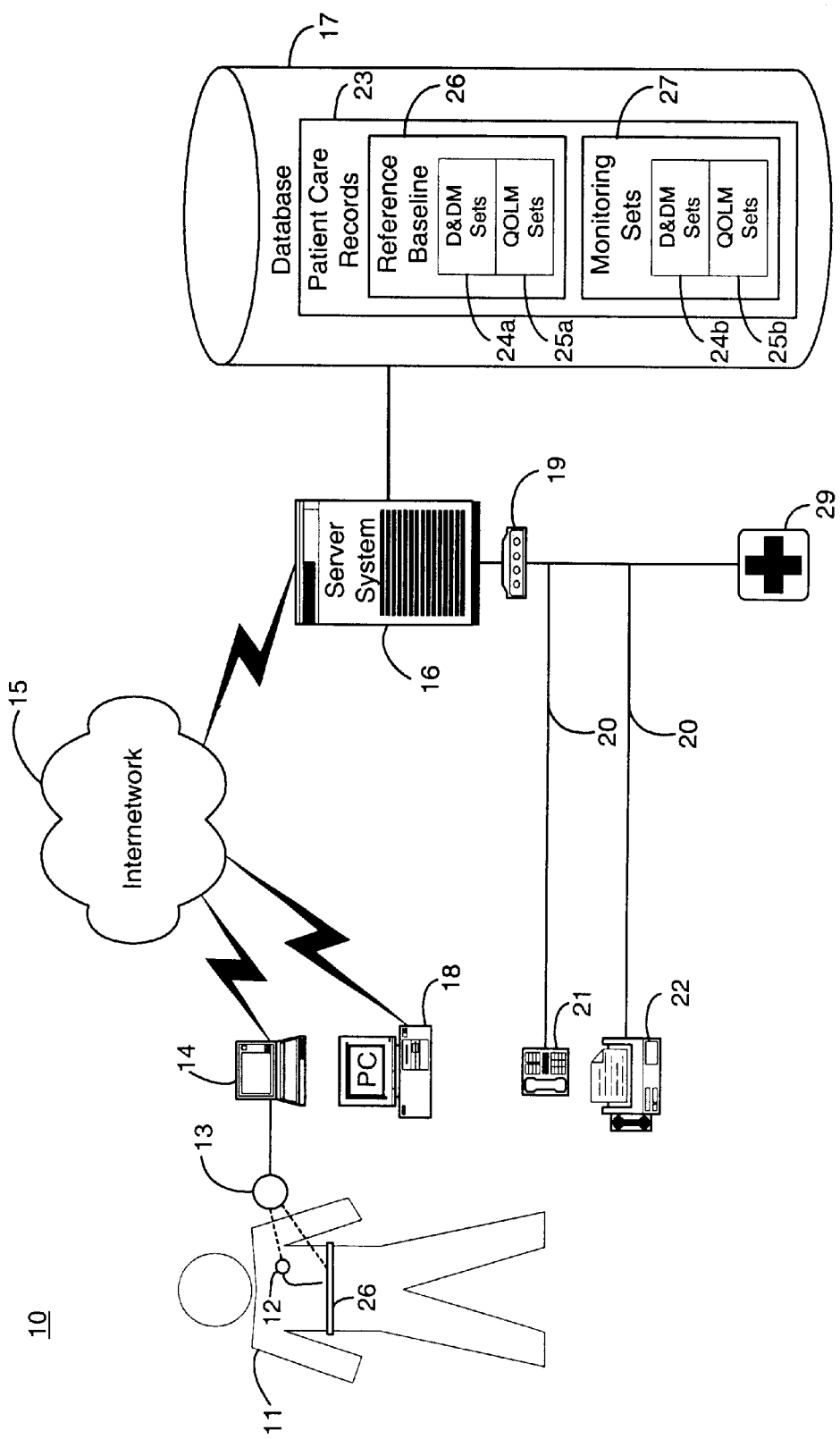
FIG. 1 is a block diagram showing an automated collection and analysis patient care system for diagnosing and monitoring the outcomes of atrial fibrillation in accordance with the present invention.

FIG. 1 is a block diagram showing an automated collection and analysis patient care system 10 for diagnosing and monitoring the outcomes of atrial fibrillation in accordance with the present invention. An exemplary automated collection and analysis patient care system suitable for use with the present invention is disclosed in the related, commonly-owned U.S. patent application Ser. No. 09/324,894, pending, filed Jun. 3, 1999, the disclosure of which is incorporated herein by reference. Preferably, an individual patient 11 is a recipient of an implantable medical device 12, such as, by way of example, an IPG, cardiovascular or heart failure monitor, or therapeutic device, with a set of leads extending into his or her heart and electrodes implanted throughout the cardiopulmonary system. In the described embodiment, an implantable anti-arrhythmia device capable of diagnosing and treating arrhythmias can be used, such as disclosed in U.S. Pat. No. 5,931,857 to Prieve et al. and U.S. Pat. No. 5,855,593 to Olson et al. Alternatively, an external monitoring or therapeutic medical device 26, a subcutaneous monitor or device inserted into other organs, a cutaneous monitor, or even a manual physiological measurement device, such as an electrocardiogram or heart rate monitor, could be used. The implantable medical device 12 and external medical device 26 include circuitry for recording into a short-term, volatile memory telemetered signals stored for later retrieval, which become part of a set of device and derived measures, such as described below, by way of example, with reference to FIG. 2. Exemplary implantable medical devices suitable for use in the present invention include the Discovery line of pacemakers, manufactured by Guidant Corporation, Indianapolis, Ind., and the Gem line of ICDs, manufactured by Medtronic Corporation, Minneapolis, Minn.

The telemetered signals stored in the implantable medical device 12 are preferably retrieved upon the completion of an initial observation period and subsequently thereafter on a continuous, periodic (daily) basis, such as described in the related, commonly-owned U.S. patent application, Ser. No. 09/361,332, pending, filed Jul. 26, 1999, the disclosure of which is incorporated herein by reference. A programmer 14, personal computer 18, or similar device for communicating with an implantable medical device 12 can be used to retrieve the telemetered signals. A magnetized reed switch (not shown) within the implantable medical device 12 closes in response to the placement of a wand 13 over the site of the implantable medical device 12. The programmer 14 sends programming or interrogating instructions to and retrieves stored telemetered signals from the implantable medical device 12 via RF signals exchanged through the wand 13. Similar communication means are used for accessing the external medical device 26. Once downloaded, the telemetered signals are sent via an internetwork 15, such as the Internet, to a server system 16 which periodically receives and stores the telemetered signals as device measures in patient care records 23 in a database 17, as further described below, by way of example, with reference to FIGS. 2 and 3. An exemplary programmer 14 suitable for use in the present invention is the Model 2901 Programmer Recorder Monitor, manufactured by Guidant Corporation, Indianapolis, Ind.

The patient 11 is remotely monitored by the server system 16 via the internetwork 15 through the periodic receipt of the retrieved device measures from the implantable medical device 12 or external medical device 26. The patient care records 23 in the database 17 are organized into two identified sets of device measures: an optional reference baseline 26 recorded during an initial observation period and monitoring sets 27 recorded subsequently thereafter. The device measures sets are periodically analyzed and compared by the server system 16 to indicator thresholds corresponding to quantifiable physiological measures of a pathophysiology resulting from atrial fibrillation and any related comorbidities, as further described below with reference to FIG. 5. As necessary, feedback is provided to the patient 11. By way of example, the feedback includes an electronic mail message automatically sent by the server system 16 over the internetwork 15 to a personal computer 18 (PC) situated for local access by the patient 11. Alternatively, the feedback can be sent through a telephone interface device 19 as an automated voice mail message to a telephone 21 or as an automated facsimile message to a facsimile machine 22, both also situated for local access by the patient 11. Moreover, simultaneous notifications can also be delivered to the patient's physician, hospital, or emergency medical services provider 29 using similar feedback means to deliver the information.

The server system 10 can consist of either a single computer system or a cooperatively networked or clustered set of computer systems. Each computer system is a general purpose, programmed digital computing device consisting of a central processing unit (CPU), random access memory (RAM), non-volatile secondary storage, such as a hard drive or CD ROM drive, network interfaces, and peripheral devices, including user interfacing means, such as a keyboard and display. Program code, including software programs, and data are loaded into the RAM for execution and processing by the CPU and results are generated for display, output, transmittal, or storage, as is known in the art.

The database 17 stores patient care records 23 for each individual patient to whom remote patient care is being provided. Each patient care record 23 contains normal patient identification and treatment profile information, as well as medical history, medications taken, height and weight, and other pertinent data (not shown). The patient care records 23 consist primarily of two sets of data: device and derived measures (D&DM) sets 24a, 24b and quality of life (QOL) and symptom measures sets 25a, 25b, the organization of which are further described below with respect to FIGS. 2 and 3, respectively. The device and derived measures sets 24a, 24b and quality of life and symptom measures sets 25a, 25b can be further logically categorized into two potentially overlapping sets. The reference baseline 26 is a special set of device and derived reference measures sets 24a and quality of life and symptom measures sets 25a recorded and determined during an initial observation period. Monitoring sets 27 are device and derived measures sets 24b and quality of life and symptom measures sets 25b recorded and determined thereafter on a regular, continuous basis. Other forms of database organization are feasible.

Figure 2:
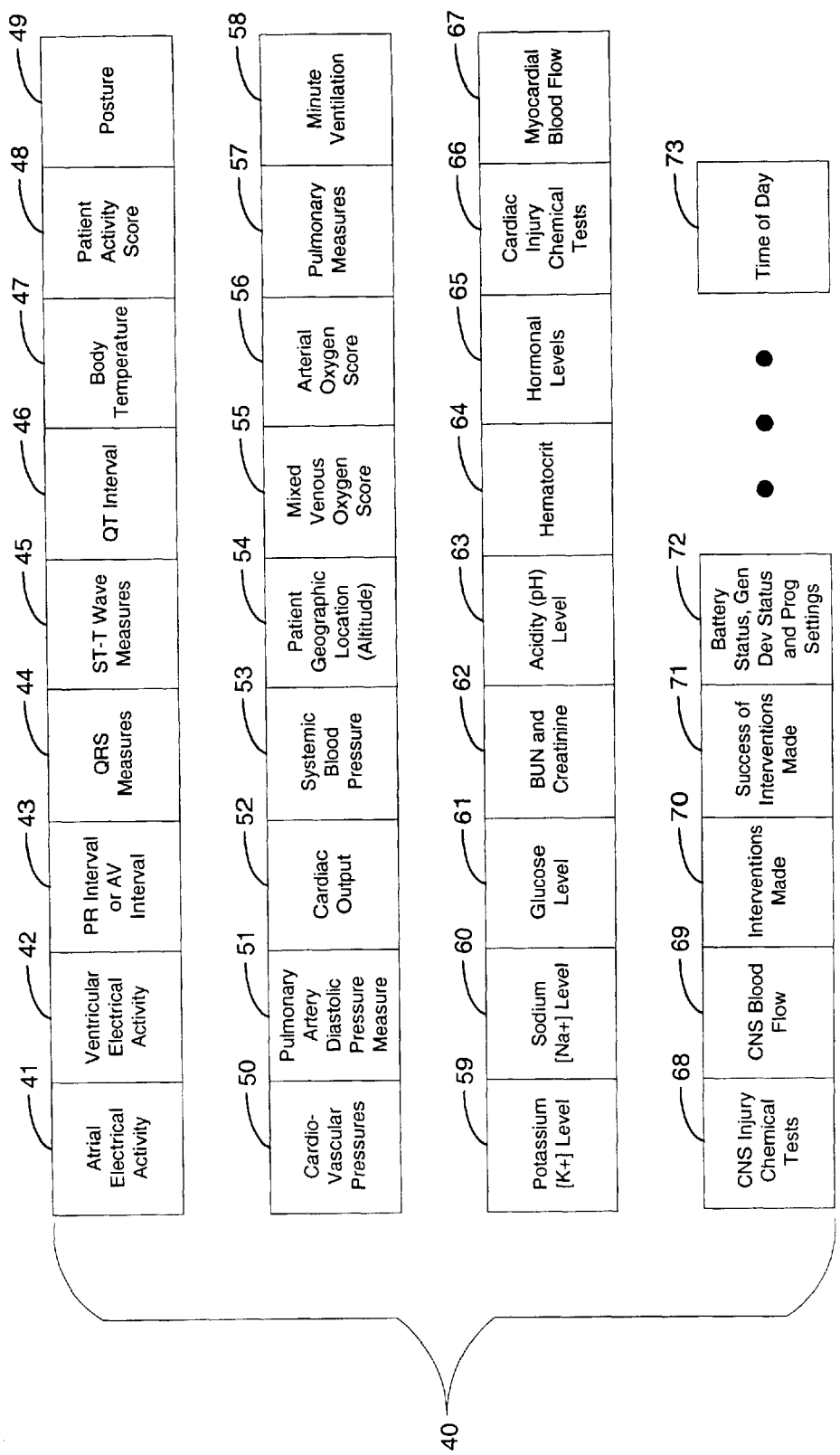
FIG. 2 is a database schema showing, by way of example, the organization of a device and derived measures set record for care of patients with atrial fibrillation stored as part of a patient care record in the database of the system of FIG. 1.

The implantable medical device 12 and, in a more limited fashion, the external medical device 26, record patient information for care of patients with atrial fibrillation on a regular basis. The recorded patient information is downloaded and stored in the database 17 as part of a patient care record 23. Further patient information can be derived from recorded data, as is known in the art. FIG. 2 is a database schema showing, by way of example, the organization of a device and derived measures set record 40 for patient care stored as part of a patient care record in the database 17 of the system of FIG. 1. Each record 40 stores patient information which includes a snapshot of telemetered signals data which were recorded by the implantable medical device 12 or the external medical device 26, for instance, on per heartbeat, binned average or derived bases; measures derived from the recorded device measures; and manually collected information, such as obtained through a patient medical history interview or questionnaire. The following non-exclusive information can be recorded for a patient: atrial electrical activity 41, ventricular electrical activity 42, PR interval or AV interval 43, QRS measures 44, ST-T wave measures 45, QT interval 46, body temperature 47, patient activity score 48, posture 49, cardiovascular pressures 50, pulmonary artery diastolic pressure measure 51, cardiac output 52, systemic blood pressure 53, patient geographic location and location (altitude) 54, mixed venous oxygen score 55, arterial oxygen score 56, pulmonary measures 57, minute ventilation 58, potassium [K+] level 59, sodium [Na+] level 60, glucose level 61, blood urea nitrogen (BUN) and creatinine 62, acidity (pH) level 63, hematocrit 64, hormonal levels 65, cardiac injury chemical tests 66, myocardial blood flow 67, central nervous system (CNS) injury chemical tests 68, central nervous system blood flow 69, interventions made by the implantable medical device or external medical device 70, and the relative success of any interventions made 71. In addition, the implantable medical device or external medical device communicates device-specific information, including battery status, general device status and program settings 72 and the time of day 73 for the various recorded measures. Other types of collected, recorded, combined, or derived measures are possible, as is known in the art.

Figure 3:
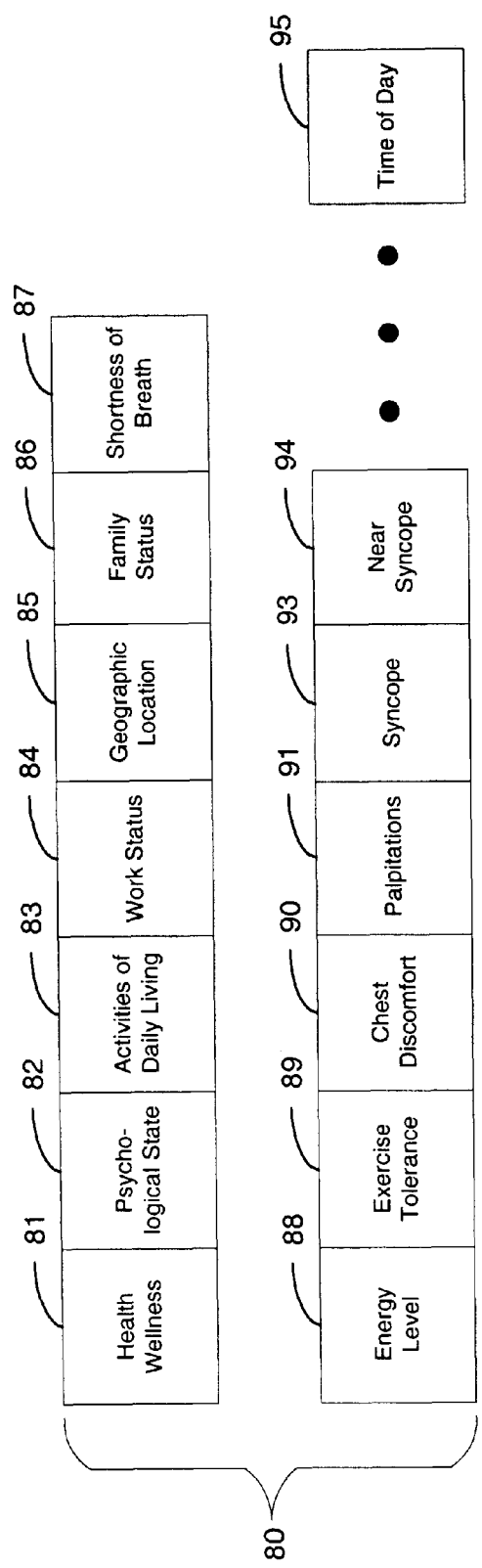
FIG. 3 is a database schema showing, by way of example, the organization of a quality of life and symptom measures set record for care of patients with atrial fibrillation stored as part of a patient care record in the database of the system of FIG. 1.

The device and derived measures sets 24a, 24b (shown in FIG. 1), along with quality of life and symptom measures sets 25a, 25b, as further described below with reference to FIG. 3, are continuously and periodically received by the server system 16 as part of the on-going patient care monitoring and analysis function. These regularly collected data sets are collectively categorized as the monitoring sets 27 (shown in FIG. 1). In addition, select device and derived measures sets 24a and quality of life and symptom measures sets 25a can be designated as a reference baseline 26 at the outset of patient care to improve the accuracy and meaningfulness of the serial monitoring sets 27. Select patient information is collected, recorded, and derived during an initial period of observation or patient care, such as described in the related, commonly-owned U.S. patent application, Ser. No. 09/361,332, pending, filed Jul. 26, 1999, the disclosure of which is incorporated herein by reference.

As an adjunct to remote patient care through the monitoring of measured physiological data via the implantable medical device 12 or external medical device 26, quality of life and symptom measures sets 25a can also be stored in the database 17 as part of the reference baseline 26, if used, and the monitoring sets 27. A quality of life measure is a semi-quantitative self-assessment of an individual patient's physical and emotional well-being and a record of symptoms, such as provided by the Duke Activities Status Indicator. These scoring systems can be provided for use by the patient 11 on the personal computer 18 (shown in FIG. 1) to record his or her quality of life scores for both initial and periodic download to the server system 16. FIG. 3 is a database schema showing, by way of example, the organization of a quality of life record 80 for use in the database 17. The following information is recorded for a patient: overall health wellness 81, psychological state 82, activities of daily living 83, work status 84, geographic location 85, family status 86, shortness of breath 87, energy level 88, exercise tolerance 89, chest discomfort 90, palpitations 91, syncope 92, near syncope 93, time of day 94, and other quality of life and symptom measures as would be known to one skilled in the art.

Other types of quality of life and symptom measures are possible, such as those indicated by responses to the Minnesota Living with Heart Failure Questionnaire described in E. Braunwald, ed., "Heart Disease—A Textbook of Cardiovascular Medicine," pp. 452–454, W. B. Saunders Co. (1997), the disclosure of which is incorporated herein by reference. Similarly, functional classifications based on the relationship between symptoms and the amount of effort required to provoke them can serve as quality of life and symptom measures, such as the New York Heart Association (NYHA) classifications I, II, III and IV, also described in Ibid.

The patient may also add non-device quantitative measures, such as the six-minute walk distance, as complementary data to the device and derived measures sets 24a, 24b and the symptoms associated with the six minute walk to the quality of life and symptom measures sets 25a, 25b.

Figure 4:
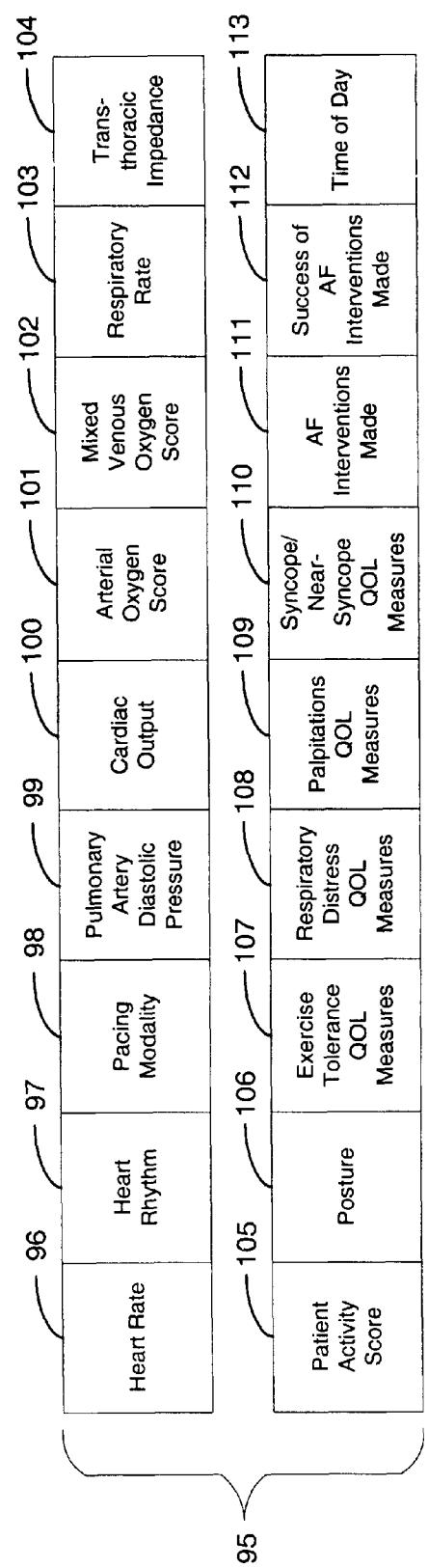
FIG. 4 is a database schema showing, by way of example, the organization of a combined measures set record for care of patients with atrial fibrillation stored as part of a patient care record in the database of the system of FIG. 1.
Figure 5:
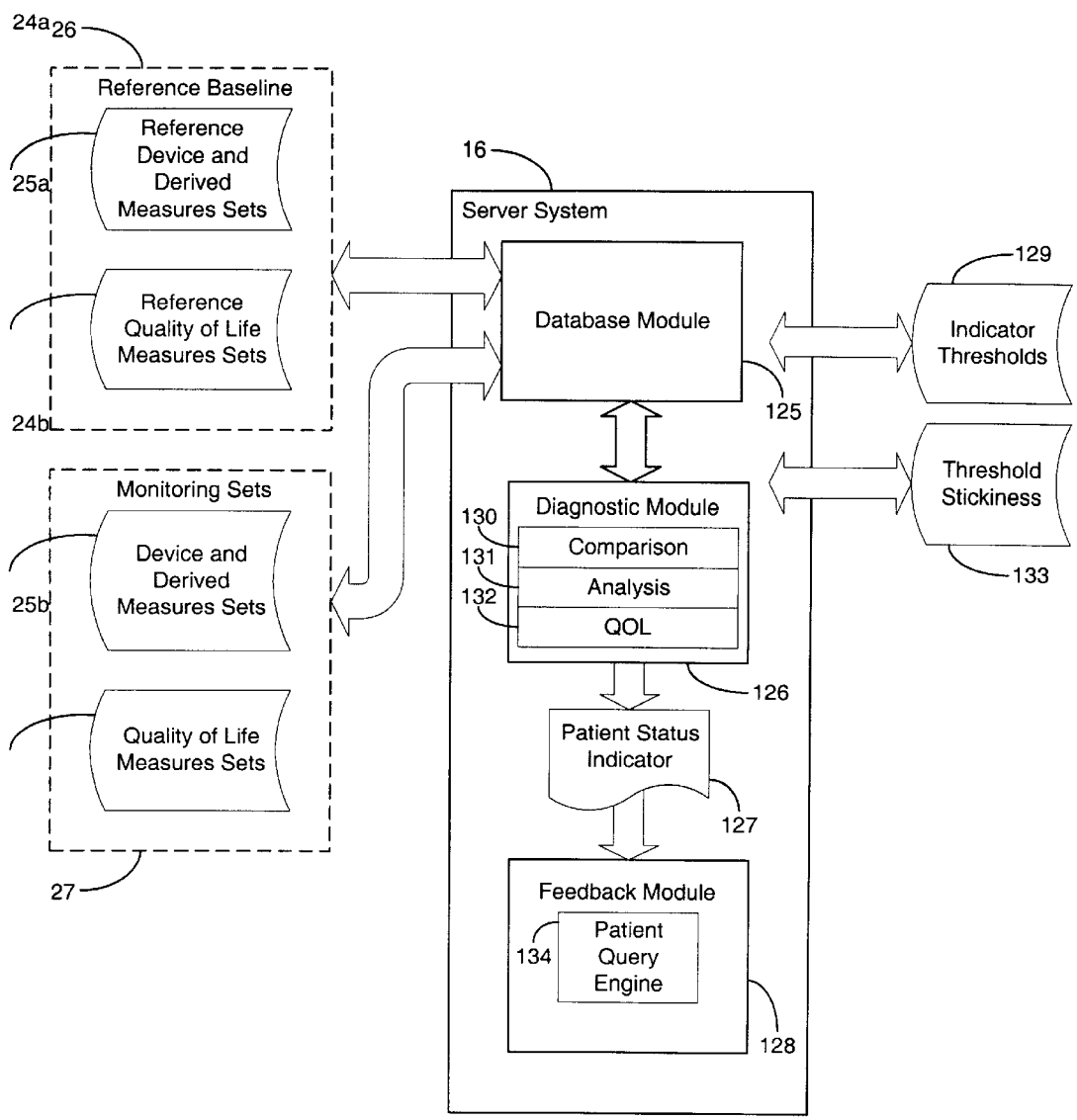
FIG. 5 is a block diagram showing the software modules of the server system of the system of FIG. 1.

On a periodic basis, the patient information stored in the database 17 is analyzed and compared to pre-determined cutoff levels, which, when exceeded, can provide etiological indications of atrial fibrillation symptoms. FIG. 4 is a database schema showing, by way of example, the organization of a combined measures set record 95 for use in the database 17. Each record 95 stores patient information obtained or derived from the device and derived measures sets 24a, 24b and quality of life and symptom measures sets 25a, 25b as maintained in the reference baseline 26, if used, and the monitoring sets 27. The combined measures set 95 represents those measures most (but not exhaustively or exclusively) relevant to a pathophysiology resulting from atrial fibrillation and are determined as further described below with reference to FIGS. 8A–8B. The following information is stored for a patient: heart rate 96, heart rhythm (e.g., normal sinus vs. atrial fibrillation) 97, pacing modality 98, pulmonary artery diastolic pressure 99, cardiac output 100, arterial oxygen score 101, mixed venous oxygen score 102, respiratory rate 103, transthoracic impedance 104, patient activity score 105, posture 106, exercise tolerance quality of life and symptom measures 107, respiratory distress quality of life and symptom measures 108, palpitations quality of life measures 109, syncope/near syncope quality of life measures 110, any interventions made to treat atrial fibrillation 111, including treatment by medical device, via drug infusion administered by the patient or by a medical device, surgery, and any other form of medical intervention as is known in the art, the relative success of any such interventions made 112, and date and time of day 113. Other types of comparison measures regarding atrial fibrillation are possible as is known in the art. In the described embodiment, each combined measures set 95 is sequentially retrieved from the database 17 and processed. Alternatively, each combined measures set 95 could be stored within a dynamic data structure maintained transitorily in the random access memory of the server system 16 during the analysis and comparison operations. FIG. 5 is a block diagram showing the software modules of the server system 16 of the system 10 of FIG. 1. Each module is a computer program written as source code in a conventional programming language, such as the C or Java programming languages, and is presented for execution by the CPU of the server system 16 as object or byte code, as is known in the art. The various implementations of the source code and object and byte codes can be held on a computer-readable storage medium or embodied on a transmission medium in a carrier wave. The server system 16 includes three primary software modules, database module 125, diagnostic module 126, and feedback module 128, which perform integrated functions as follows.

First, the database module 125 organizes the individual patient care records 23 stored in the database 17 (shown in FIG. 1) and efficiently stores and accesses the reference baseline 26, monitoring sets 27, and patient care data maintained in those records. Any type of database organization could be utilized, including a flat file system, hierarchical database, relational database, or distributed database, such as provided by database vendors, such as Oracle Corporation, Redwood Shores, Calif.

Next, the diagnostic module 126 makes findings of atrial fibrillation and attendant cardiovascular consequences through the implantable medical device 12 and, in a more limited fashion, the external medical device 26, and categorizes the findings into reduced exercise capacity-, respiratory distress-, palpitations-, and syncope/near syncope-related atrial fibrillation based on the comparison and analysis of the data measures from the reference baseline 26 and monitoring sets 27. The diagnostic module includes three modules: comparison module 130, analysis module 131, and quality of life module 132. The comparison module 130 compares recorded and derived measures retrieved from the reference baseline 26, if used, and monitoring sets 27 to indicator thresholds 129. The database 17 stores individual patient care records 23 for patients suffering from various health disorders and diseases for which they are receiving remote patient care. For purposes of comparison and analysis by the comparison module 130, these records can be categorized into peer groups containing the records for those patients suffering from similar disorders, as well as being viewed in reference to the overall patient population. The definition of the peer group can be progressively refined as the overall patient population grows. To illustrate, FIG. 6 is a record view showing, by way of example, a set of partial patient care records for care of patients with atrial fibrillation stored in the database 17 for three patients, Patient 1, Patient 2, and Patient 3. For each patient, three sets of peer measures, X, Y, and Z, are shown. Each of the measures, X, Y, and Z, could be either collected or derived measures from the reference baseline 26, if used, and monitoring sets 27.

The same measures are organized into time-based sets with Set 0 representing sibling measures made at a reference time t=0. Similarly, Set n−2, Set n−1 and Set n each represent sibling measures made at later reference times t=n−2, t=n−1 and t=n, respectively. Thus, for a given patient, such as Patient 1, serial peer measures, such as peer measure $X_0$ through $X_n$, represent the same type of patient information monitored over time. The combined peer measures for all patients can be categorized into a health disorder- or disease-matched peer group. The definition of disease-matched peer group is a progressive definition, refined over time as the number of monitored patients grows. Measures representing different types of patient information, such as measures $X_0$, $Y_0$, and $Z_0$, are sibling measures. These are measures which are also measured over time, but which might have medically significant meaning when compared to each other within a set for an individual patient.

The comparison module 130 performs two basic forms of comparison. First, individual measures for a given patient can be compared to other individual measures for that same patient (self-referencing). These comparisons might be peer-to-peer measures, that is, measures relating to a one specific type of patient information, projected over time, for instance, $X_n$, $X_{n-1}$, $X_{n-2}$, . . . $X_0$, or sibling-to-sibling measures, that is, measures relating to multiple types of patient information measured during the same time period, for a single snapshot, for instance, $X_n$, $Y_n$, and $Z_n$, or projected over time, for instance, $X_n$, $Y_n$, $Z_n$, $X_{n-1}$, $Y_{n-1}$, $Z_{n-1}$, $X_{n-2}$, $Y_{n-2}$, $Z_{n-2}$, . . . $X_0$, $Y_0$, $Z_0$. Second, individual measures for a given patient can be compared to other individual measures for a group of other patients sharing the same disorder- or disease-specific characteristics (peer group referencing) or to the patient population in general (population referencing). Again, these comparisons might be peer-to-peer measures projected over time, for instance, $X_n$, $X_{n'}$, $X_{n''}$, $X_{n-1}$, $X_{n-1'}$, $X_{n-1''}$, $X_{n-2}$, $X_{n-2'}$, $X_{n-2''}$, . . . $X_0$, $X_{0'}$, $X_{0''}$, or comparing the individual patient's measures to an average from the group. Similarly, these comparisons might be sibling-to-sibling measures for single snapshots, for instance, $X_n$, $X_{n'}$, $X_{n''}$, $Y_n$, $Y_{n'}$, $Y_{n''}$, and $Z_n$, $Z_{n'}$, $Z_{n''}$, or projected over time, for instance, $X_n$, $X_{n'}$, $X_{n''}$, $Y_n$, $Y_{n'}$, $Y_{n''}$, $Z_n$, $Z_{n'}$, $Z_{n''}$, $X_{n-1}$, $X_{n-1'}$, $X_{n-1''}$, $Y_{n-1}$, $Y_{n-1'}$, $Y_{n-1''}$, $Z_{n-1}$, $Z_{n-1'}$, $Z_{n-1''}$, $X_{n-2}$, $X_{n-2'}$, $X_{n-2''}$, $Y_{n-2}$, $Y_{n-2'}$, $Y_{n-2''}$, $Z_{n-2}$, $Z_{n-2'}$, $Z_{n-2''}$. . . $X_0$, $X_{0'}$, $X_{0''}$, $Y_0$, $Y_{0'}$, $Y_{0''}$, and $Z_0$, $Z_{0'}$, $Z_{0''}$. Other forms of comparisons are feasible, including multiple disease diagnoses for diseases exhibiting similar abnormalities in physiological measures that might result from a second disease but manifest in different combinations or onset in different temporal sequences.

Figure 7:
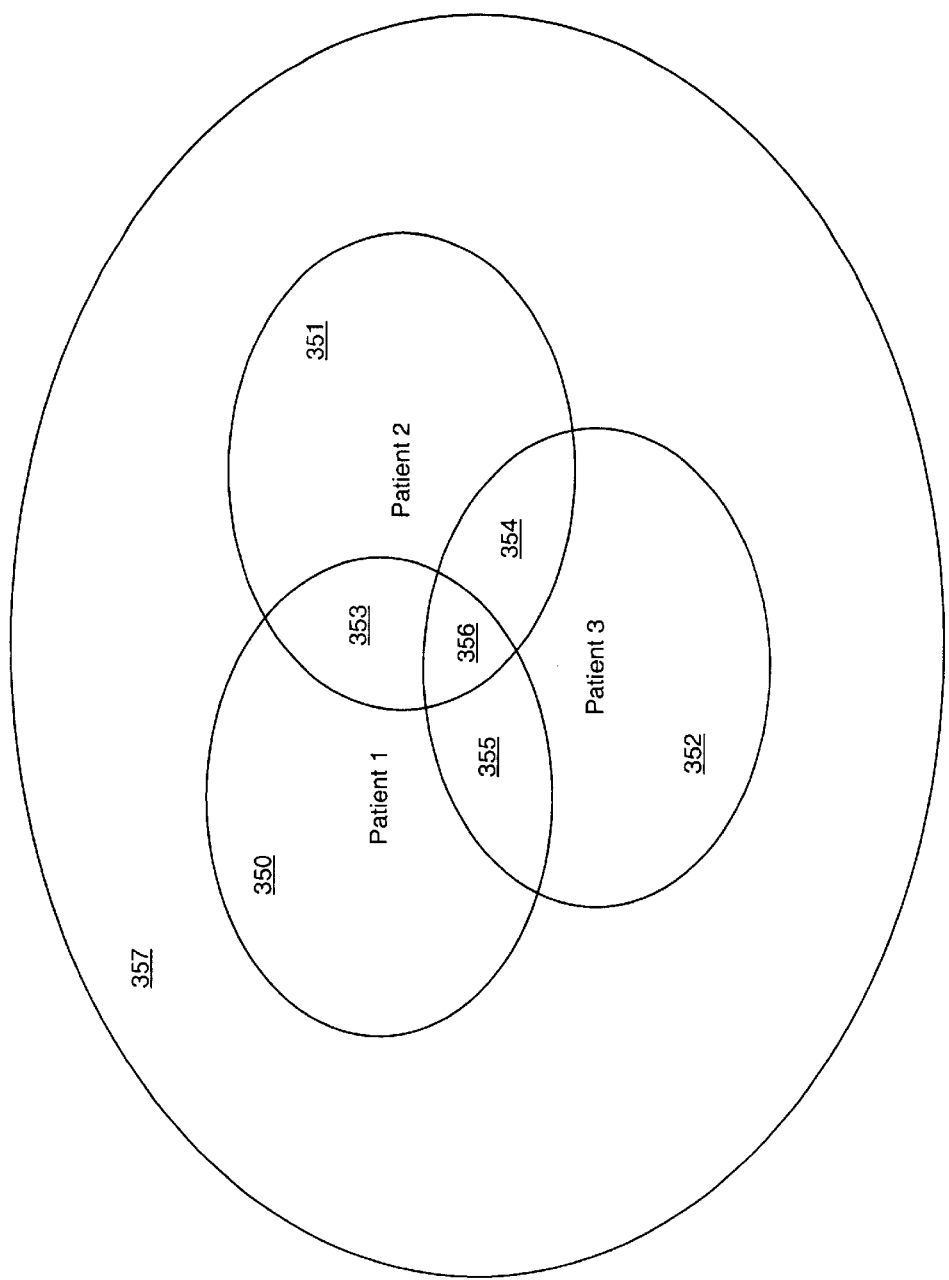
FIG. 7 is a Venn diagram showing, by way of example, peer group overlap between the partial patient care records of FIG. 6.

FIG. 7 is a Venn diagram showing, by way of example, peer group overlap between the partial patient care records 23 of FIG. 1. Each patient care record 23 includes characteristics data 350, 351, 352, including personal traits, demographics, medical history, and related personal data, for patients 1, 2 and 3, respectively. For example, the characteristics data 350 for patient 1 might include personal traits which include gender and age, such as male and an age between 40–45; a demographic of resident of New York City; and a medical history consisting of anterior myocardial infraction, paroxysmal atrial fibrillation and diabetes. Similarly, the characteristics data 351 for patient 2 might include identical personal traits, thereby resulting in partial overlap 353 of characteristics data 350 and 351. Similar characteristics overlap 354, 355, 356 can exist between each respective patient. The overall patient population 357 would include the universe of all characteristics data. As the monitoring population grows, the number of patients with personal traits matching those of the monitored patient will grow, increasing the value of peer group referencing. Large peer groups, well matched across all monitored measures, will result in a well known natural history of disease and will allow for more accurate prediction of the clinical course of the patient being monitored. If the population of patients is relatively small, only some traits 356 will be uniformly present in any particular peer group. Eventually, peer groups, for instance, composed of 100 or more patients each, would evolve under conditions in which there would be complete overlap of substantially all salient data, thereby forming a powerful core reference group for any new patient being monitored.

Referring back to FIG. 5, the analysis module 131 analyzes the results from the comparison module 130, which are stored as a combined measures set 95 (not shown), to a set of indicator thresholds 129, as further described below with reference to FIGS. 8A–8B. Similarly, the quality of life module 132 compares quality of life and symptom measures set 25a, 25b from the reference baseline 26 and monitoring sets 27, the results of which are incorporated into the comparisons performed by the analysis module 131, in part, to either refute or support the findings based on physiological "hard" data. Finally, the feedback module 128 provides automated feedback to the individual patient based, in part, on the patient status indicator 127 generated by the diagnostic module 126. As described above, the feedback could be by electronic mail or by automated voice mail or facsimile. The feedback can also include normalized voice feedback, such as described in the related, commonly-owned U.S. patent application, Ser. No. 09/361,777, pending, filed Jul. 26, 1999, the disclosure of which is incorporated herein by reference. In addition, the feedback module 128 determines whether any changes to interventive measures are appropriate based on threshold stickiness ("hysteresis") 133, as further described below with reference to FIG. 16. The threshold stickiness 133 can prevent fickleness in diagnostic routines resulting from transient, non-trending and non-significant fluctuations in the various collected and derived measures in favor of more certainty in diagnosis. In a further embodiment of the present invention, the feedback module 128 includes a patient query engine 134 which enables the individual patient 11 to interactively query the server system 16 regarding the diagnosis, therapeutic maneuvers, and treatment regimen. Conversely, the patient query engines 134, found in interactive expert systems for diagnosing medical conditions, can interactively query the patient. Using the personal computer 18 (shown in FIG. 1), the patient can have an interactive dialogue with the automated server system 16, as well as human experts as necessary, to self assess his or her medical condition. Such expert systems are well known in the art, an example of which is the MYCIN expert system developed at Stanford University and described in Buchanan, B. & Shortlife, E., "RULE-BASED EXPERT SYSTEMS. The MYCIN Experiments of the Stanford Heuristic Programming Project," Addison-Wesley (1984). The various forms of feedback described above help to increase the accuracy and specificity of the reporting of the quality of life and symptomatic measures.

Figure 8A:
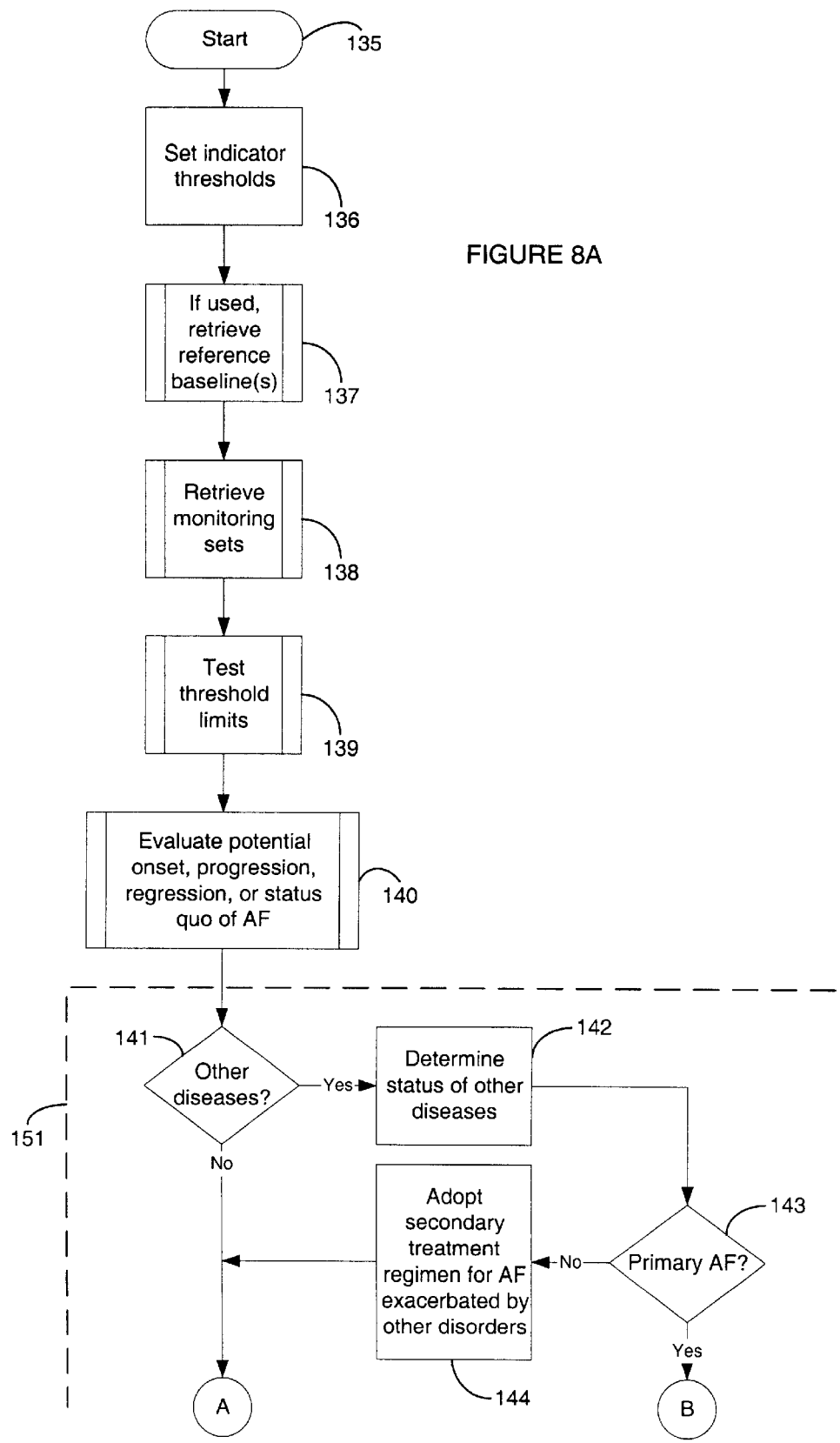
FIGS. 8A–8B are flow diagrams showing a method for diagnosing and monitoring the outcomes of atrial fibrillation using an automated collection and analysis patient care system in accordance with the present invention.
Figure 8B:
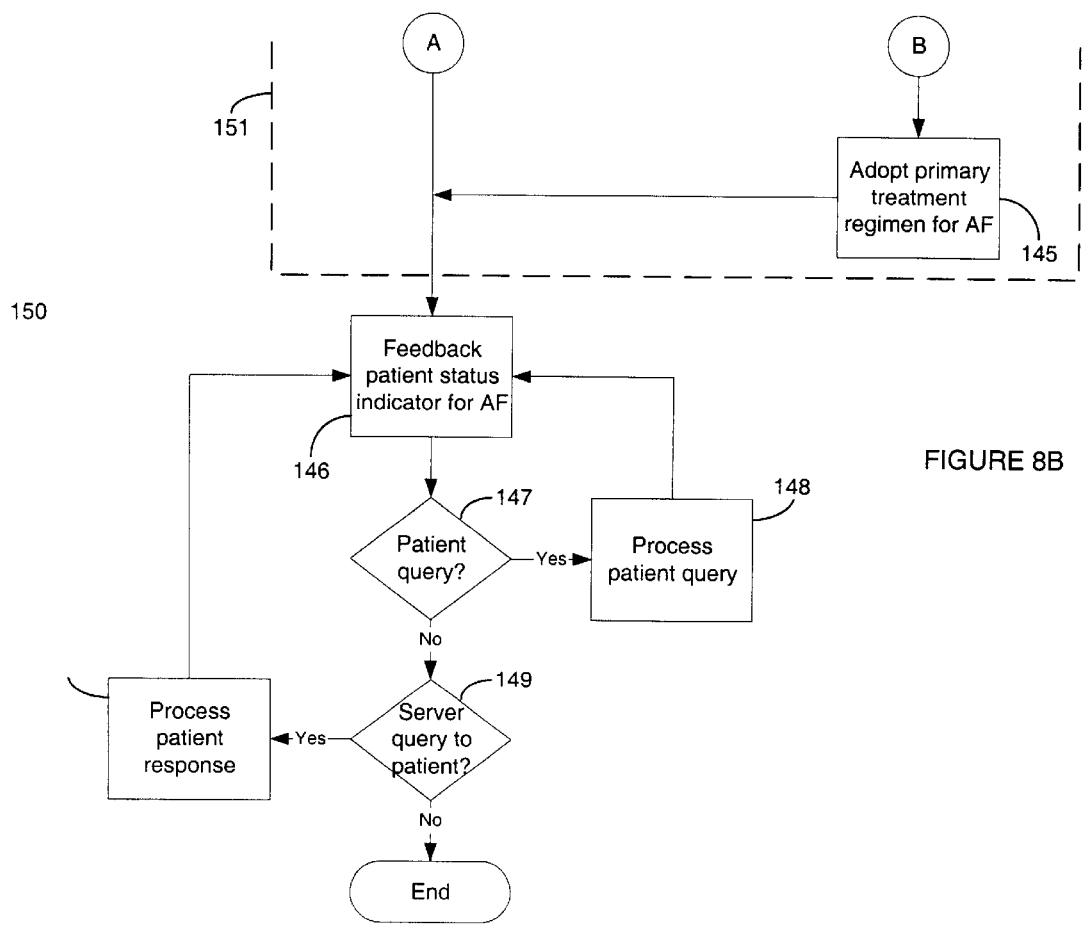

FIGS. 8A–8B are flow diagrams showing a method for diagnosing and monitoring the outcomes of atrial fibrillation 135 using an automated collection and analysis patient care system 10 in accordance with the present invention. First, the indicator thresholds 129 (shown in FIG. 5) are set (block 136) by defining a quantifiable physiological measure of a pathophysiology resulting from atrial fibrillation and relating to each type of patient information in the combined device and derived measures set 95 (shown in FIG. 4). The actual values of each indicator threshold can be finite cutoff values, weighted values, or statistical ranges, as discussed below with reference to FIGS. 11A–11D. Next, the reference baseline 26 (block 137) and monitoring sets 27 (block 138) are retrieved from the database 17, as further described below with reference to FIGS. 9 and 10, respectively. Each measure in the combined device and derived measures set 95 is tested against the threshold limits defined for each indicator threshold 129 (block 139), as further described below with reference to FIGS. 11A–11D. The potential onset, progression (where progression of atrial fibrillation is defined as a ventricular rate increase and/or a deterioration in physiological cardiovascular and cardiopulmonary measures regardless of rate change), regression (where regression of atrial fibrillation is defined as its offset, a decrease in ventricular rate, and/or an improvement in cardiovascular and cardiopulmonary physiological measures), or status quo of atrial fibrillation is then evaluated (block 140) based upon the findings of the threshold limits tests (block 139), as further described below with reference to FIGS. 13A–13B, 14A–14B, 15A–15B.

In a further embodiment, multiple near-simultaneous disorders are considered in addition to primary atrial fibrillation. Primary atrial fibrillation is defined as the onset or progression of atrial fibrillation without obvious inciting identifiable cause. Secondary atrial fibrillation is defined as the onset or progression of atrial fibrillation (in a patient with or without a history of previously documented atrial fibrillation) from another disease process, such as congestive heart failure, myocardial ischemia, coronary insufficiency, respiratory insufficiency, specific identifiable electrophysiological abnormalities, and so forth. Other health disorders and diseases can potentially share the same forms of symptomatology as atrial fibrillation, such as myocardial ischemia, respiratory insufficiency, pneumonia, exacerbation of chronic bronchitis, renal failure, sleep-apnea, stroke, anemia, other cardiac arrhythmias, and so forth. If more than one abnormality is present, the relative sequence and magnitude of onset of abnormalities in the monitored measures becomes most important in sorting and prioritizing disease diagnosis and treatment.

Thus, if other disorders or diseases are being cross-referenced and diagnosed (block 141), their status is determined (block 142). In the described embodiment, the operations of ordering and prioritizing multiple near-simultaneous disorders (box 151) by the testing of threshold limits and analysis in a manner similar to congestive heart failure as described above, preferably in parallel to the present determination, is described in the related, commonly-owned U.S. patent application, Ser. No. 09/441,405, entitled "Automated Collection And Analysis Patient Care System And Method For Ordering And Prioritizing Multiple Health Disorders To Identify An Index Disorder," pending, filed Nov. 16, 1999, the disclosure of which is incorporated herein by reference. If atrial fibrillation is due to an obvious inciting cause, i.e., secondary atrial fibrillation, (block 143), an appropriate treatment regimen is adopted that includes treatment of secondary disorders, e.g., myocardial ischemia, respiratory insufficiency, and so forth (block 144), as well as atrial fibrillation if needed, and a suitable patient status indicator 127 for atrial fibrillation is provided (block 146) to the patient indicating diagnosis and management recommendations for both atrial fibrillation and inciting causes. Suitable devices and approaches to diagnosing and treating congestive heart failure, myocardial infarction, and respiratory insufficiency are described in related, commonly-owned U.S. patent applications, Ser. No. 09/441,624, entitled "Automated Collection And Analysis Patient Care System And Method For Diagnosing And Monitoring Congestive Heart Failure And Outcomes Thereof," pending, filed Nov. 16, 1999; Ser. No. 09/441,612, entitled "Automated Collection And Analysis Patient Care System And Method For Diagnosing And Monitoring Myocardial Ischemia And Outcomes Thereof," pending, filed Nov. 16, 1999; and Ser. No. 09/442,125, entitled "Automated Collection And Analysis Patient Care System And Method For Diagnosing And Monitoring Respiratory Insufficiency And Outcomes Thereof," pending, filed Nov. 16, 1999, the disclosures of which are incorporated herein by reference.

Otherwise, if primary atrial fibrillation is indicated (block 143), a primary treatment regimen is followed (block 145). A patient status indicator 127 for atrial fibrillation is provided (block 146) to the patient regarding physical well-being, disease prognosis, including any determinations of disease onset, progression, regression, or status quo, and other pertinent medical and general information of potential interest to the patient.

Finally, in a further embodiment, if the patient submits a query to the server system 16 (block 147), the patient query is interactively processed by the patient query engine (block 148). Similarly, if the server elects to query the patient (block 149), the server query is interactively processed by the server query engine (block 150). The method then terminates if no further patient or server queries are submitted.

Figure 9:
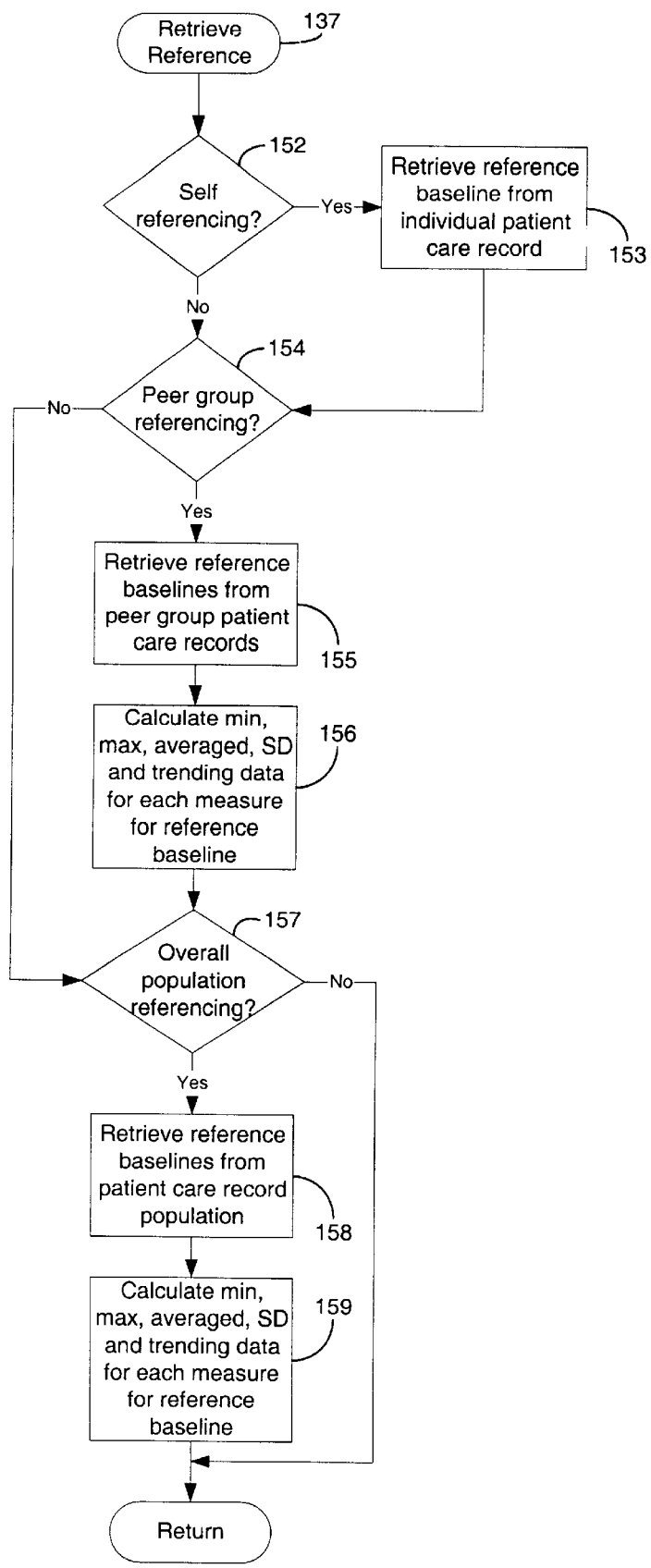
FIG. 9 is a flow diagram showing the routine for retrieving reference baseline sets for use in the method of FIGS. 8A–8B.

FIG. 9 is a flow diagram showing the routine for retrieving reference baseline sets 137 for use in the method of FIGS. 8A–8B. The purpose of this routine is to retrieve the appropriate reference baseline sets 26, if used, from the database 17 based on the types of comparisons being performed. First, if the comparisons are self referencing with respect to the measures stored in the individual patient care record 23 (block 152), the reference device and derived measures set 24a and reference quality of life and symptom measures set 25a, if used, are retrieved for the individual patient from the database 17 (block 153). Next, if the comparisons are peer group referencing with respect to measures stored in the patient care records 23 for a health disorder- or disease-specific peer group (block 154), the reference device and derived measures set 24a and reference quality of life and symptom measures set 25a, if used, are retrieved from each patient care record 23 for the peer group from the database 17 (block 155). Data for each measure (e.g., minimum, maximum, averaged, standard deviation (SD), and trending data) from the reference baseline 26 for the peer group is then calculated (block 156). Finally, if the comparisons are population referencing with respect to measures stored in the patient care records 23 for the overall patient population (block 157), the reference device and derived measures set 24a and reference quality of life and symptom measures set 25a, if used, are retrieved from each patient care record 23 from the database 17 (block 158). Minimum, maximum, averaged, standard deviation, and trending data and other numerical processes using the data, as is known in the art, for each measure from the reference baseline 26 for the peer group is then calculated (block 159). The routine then returns.

Figure 10:
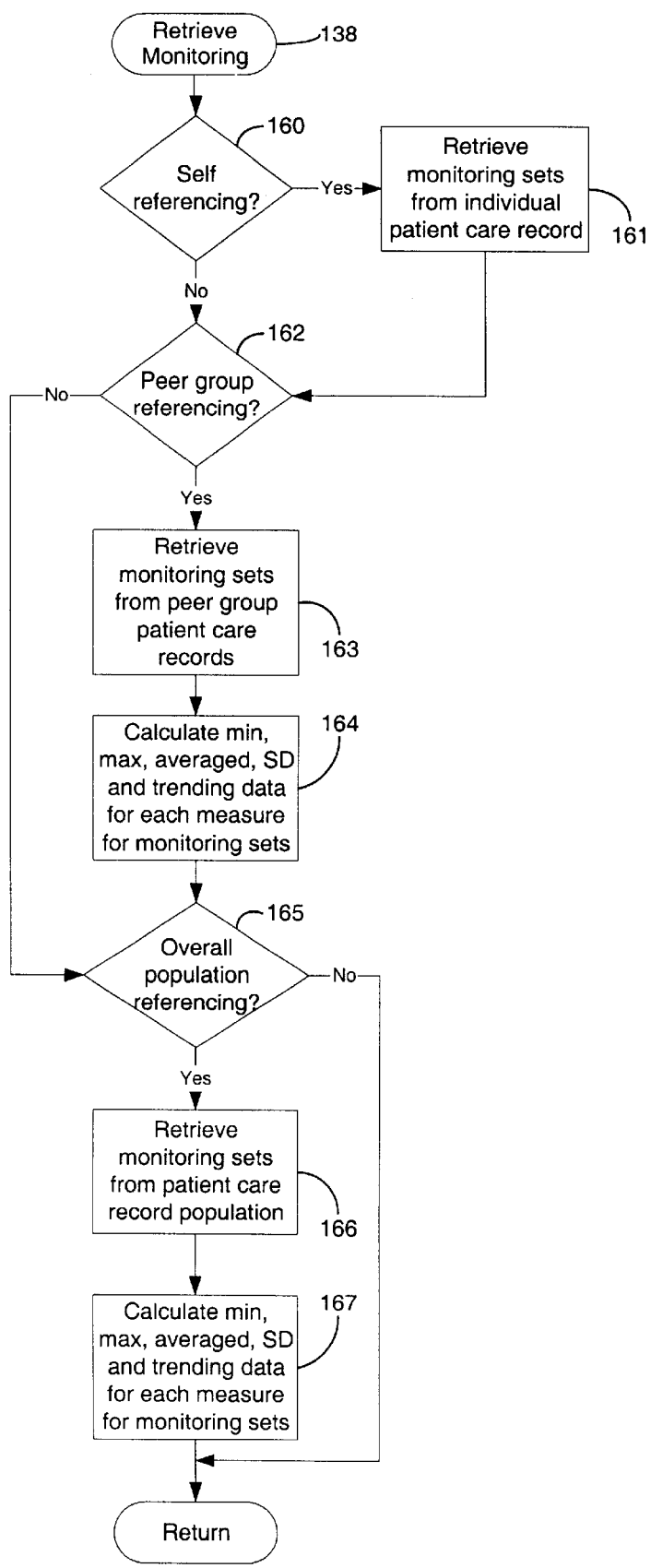
FIG. 10 is a flow diagram showing the routine for retrieving monitoring sets for use in the method of FIGS. 8A–8B.
Figure 11A:
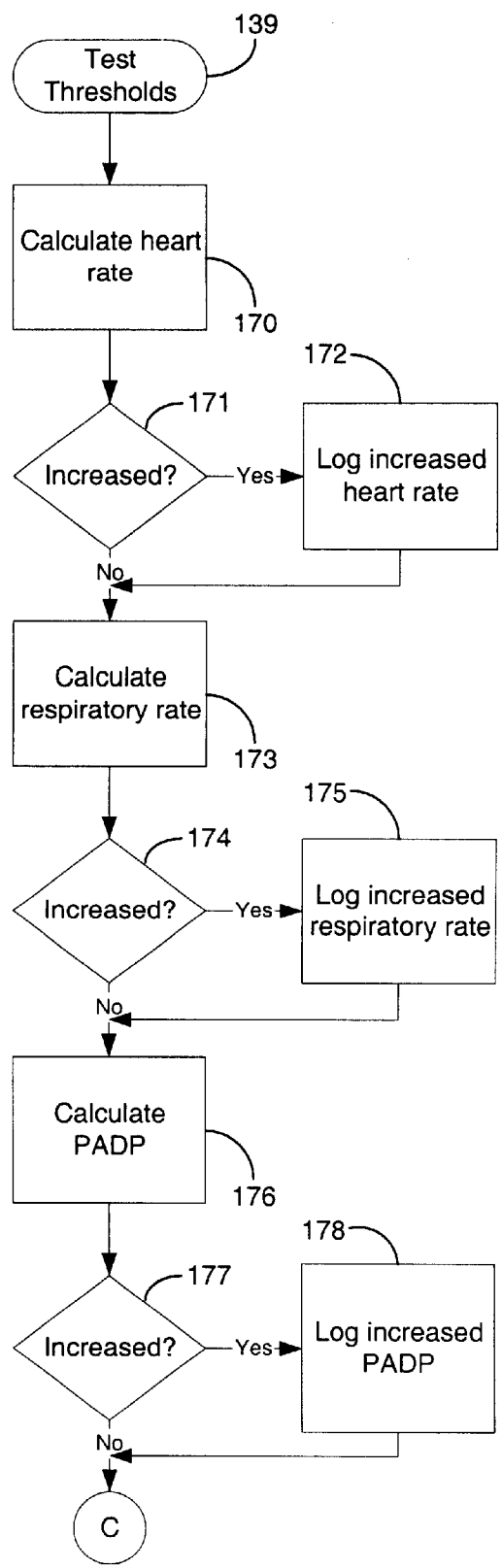
FIGS. 11A–11D are flow diagrams showing the routine for testing threshold limits for use in the method of FIGS. 8A–8B.
Figure 11B:
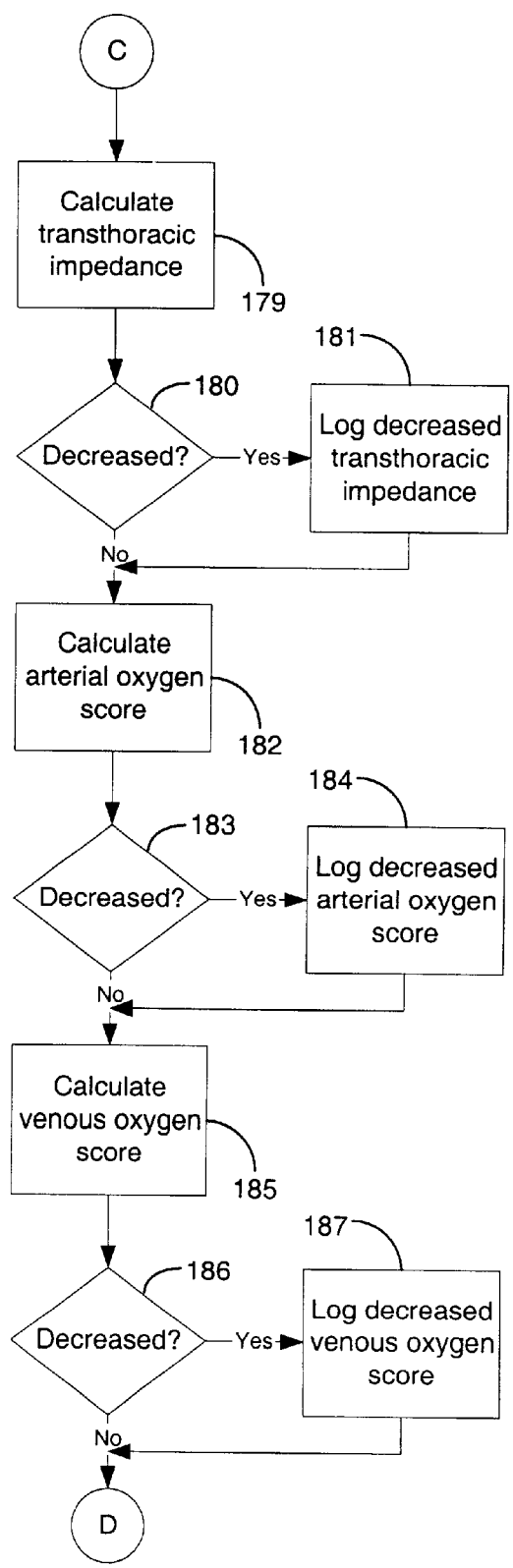
Figure 11C:
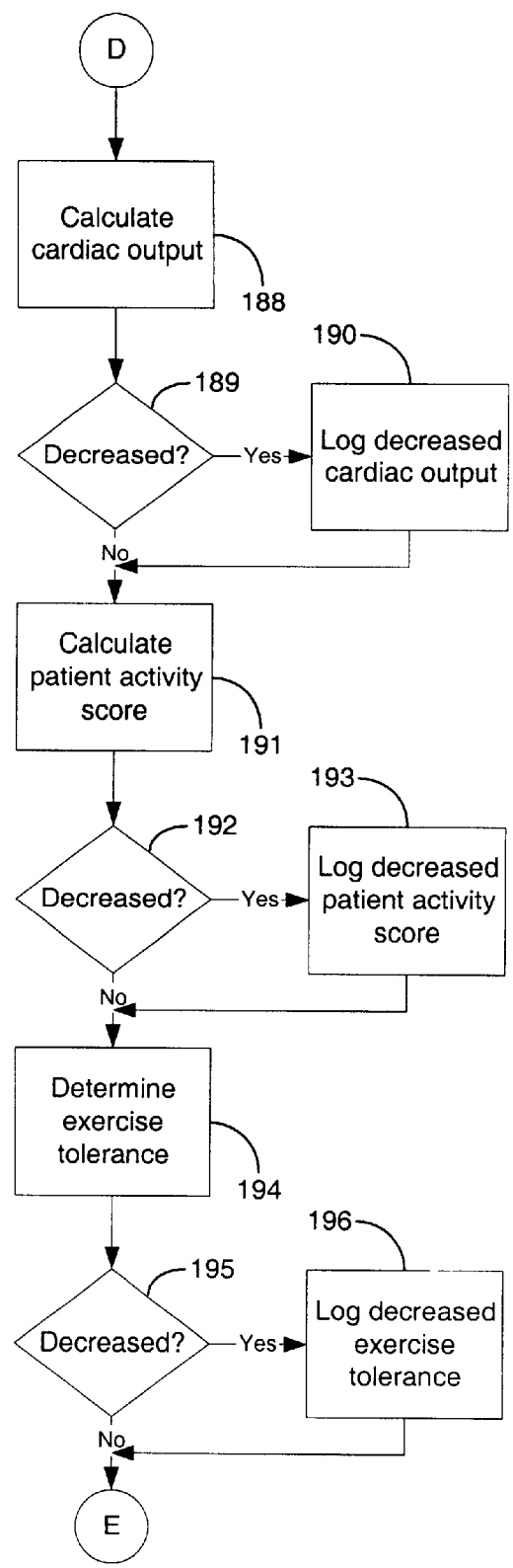
Figure 11D:
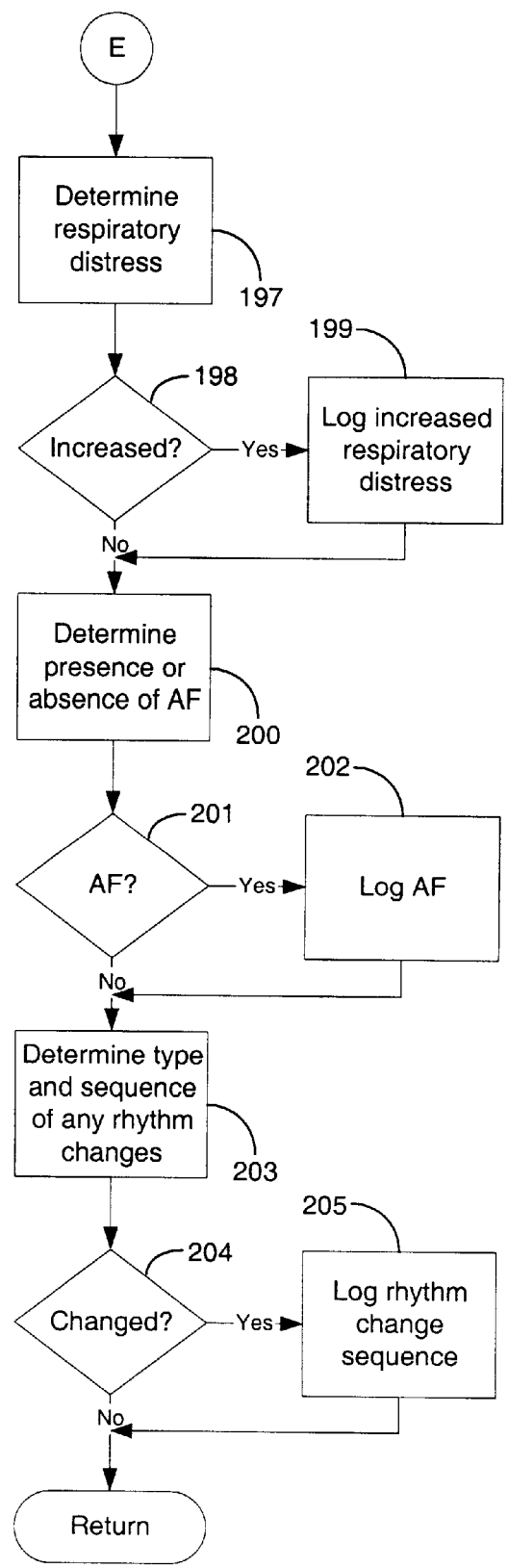

FIG. 10 is a flow diagram showing the routine for retrieving monitoring sets 138 for use in the method of FIGS. 8A–8B. The purpose of this routine is to retrieve the appropriate monitoring sets 27 from the database 17 based on the types of comparisons being performed. First, if the comparisons are self referencing with respect to the measures stored in the individual patient care record 23 (block 160), the device and derived measures set 24b and quality of life and symptom measures set 25b, if used, are retrieved for the individual patient from the database 17 (block 161). Next, if the comparisons are peer group referencing with respect to measures stored in the patient care records 23 for a health disorder- or disease-specific peer group (block 162), the device and derived measures set 24b and quality of life and symptom measures set 25b, if used, are retrieved from each patient care record 23 for the peer group from the database 17 (block 163). Data for each measure (e.g., minimum, maximum, averaged, standard deviation, and trending data) from the monitoring sets 27 for the peer group is then calculated (block 164). Finally, if the comparisons are population referencing with respect to measures stored in the patient care records 23 for the overall patient population (block 165), the device and derived measures set 24b and quality of life and symptom measures set 25b, if used, are retrieved from each patient care record 23 from the database 17 (block 166). Minimum, maximum, averaged, standard deviation, and trending data and other numerical processes using the data, as is known in the art, for each measure from the monitoring sets 27 for the peer group is then calculated (block 167). The routine then returns.

FIGS. 11A–11D are flow diagrams showing the routine for testing threshold limits 139 for use in the method of FIGS. 8A and 8B. The purpose of this routine is to analyze, compare, and log any differences between the observed, objective measures stored in the reference baseline 26, if used, and the monitoring sets 27 to the indicator thresholds 129. Briefly, the routine consists of tests pertaining to each of the indicators relevant to diagnosing and monitoring the outcomes of atrial fibrillation and cardiovascular consequences. The threshold tests focus primarily on: (1) changes to and rates of change for the indicators themselves, as stored in the combined device and derived measures set 95 (shown in FIG. 4) or similar data structure; and (2) violations of absolute threshold limits which trigger an alert. The timing and degree of change may vary with each measure and with the natural fluctuations noted in that measure during the reference baseline period. In addition, the timing and degree of change might also vary with the individual and the natural history of a measure for that patient.

One suitable approach to performing the threshold tests uses a standard statistical linear regression technique using a least squares error fit. The least squares error fit can be calculated as follows:

$$y = \beta_0 + \beta_1 x \quad (1)$$

$$\beta = \frac{SS_{xy}}{SS_{xx}} \quad (2)$$

$$SS_{xy} = \sum_{i=1}^{n} x_i y_i - \frac{\left(\sum_{i=1}^{n} x_i\right)\left(\sum_{i=1}^{n} y_i\right)}{n} \quad (3)$$

$$SS_{xx} = \sum_{i=1}^{n} x_i^2 - \frac{\left(\sum_{i=1}^{n} x_i\right)^2}{n} \quad (4)$$

where n is the total number of measures, $x_i$ is the time of day for measure i, and $y_i$ is the value of measure i, $\beta_1$ is the slope, and $\beta_0$ is the y-intercept of the least squares error line. A positive slope $\beta_1$ indicates an increasing trend, a negative slope $\beta_1$ indicates a decreasing trend, and no slope indicates no change in patient condition for that particular measure. A predicted measure value can be calculated and compared to the appropriate indicator threshold 129 for determining whether the particular measure has either exceeded an acceptable threshold rate of change or the absolute threshold limit.

For any given patient, three basic types of comparisons between individual measures stored in the monitoring sets 27 are possible: self referencing, peer group, and general population, as explained above with reference to FIG. 6. In addition, each of these comparisons can include comparisons to individual measures stored in the pertinent reference baselines 24.

The indicator thresholds 129 for detecting a trend indicating an adverse consequence of atrial fibrillation or a state of imminent or likely cardiovascular or cardiopulmonary deterioration, for example, over a one week time period, can be as follows:

(1) Heart rate (block 170): If the ventricular heart rate during atrial fibrillation has increased over 1.0 SD from the mean heart rate in the reference baseline 26, if used (block 171), the increased ventricular heart rate and time span over which it occurs are logged in the combined measures set 95 (block 172).

(2) Respiratory rate (block 173): If the respiratory rate has increased over 1.0 SD from the mean respiratory rate in the reference baseline 26, if used (block 174), the increased respiratory rate and time span over which it occurs are logged in the combined measures set 95 (block 175).

(3) Pulmonary artery diastolic pressure (PADP) (block 176) reflects left ventricular filling pressure and is a measure of left ventricular dysfunction. Ideally, the left ventricular end diastolic pressure (LVEDP) should be monitored, but in practice is difficult to measure. Consequently, without the LVEDP, the PADP, or derivatives thereof, is suitable for use as an alternative to LVEDP in the present invention. If the PADP has increased over 1.0 SD from the mean PADP in the reference baseline 26 (block 177), the increased PADP and time span over which that increase occurs, are logged in the combined measures set 95 (block 178). Other cardiac pressures or derivatives could also apply.

(4) Transthoracic impedance (block 179): If the transthoracic impedance has decreased over 1.0 SD from the mean transthoracic impedance in the reference baseline 26 (block 180), the decreased transthoracic impedance and time span are logged in the combined measures set 95 (block 181).

(5) Arterial oxygen score (block 182): If the arterial oxygen score has decreased over 1.0 SD from the arterial oxygen score in the reference baseline 26 (block 183), the decreased arterial oxygen score and time span are logged in the combined measures set 95 (block 184).

(6) Venous oxygen score (block 185): If the venous oxygen score has decreased over 1.0 SD from the mean venous oxygen score in the reference baseline 26 (block 186), the decreased venous oxygen score and time span are logged in the combined measures set 95 (block 187).

(7) Cardiac output (block 188): If the cardiac output has decreased over 1.0 SD from the mean cardiac output in the reference baseline 26 (block 189), the decreased cardiac output and time span are logged in the combined measures set 95 (block 190).

(8) Patient activity score (block 191): If the mean patient activity score has decreased over 1.0 SD from the mean patient activity score in the reference baseline 26 (block 192), the decreased patient activity score and time span are logged in the combined measures set 95 (block 193).

(9) Exercise tolerance quality of life (QOL) measures (block 194): If the exercise tolerance QOL has decreased over 1.0 SD from the mean exercise tolerance in the reference baseline 26 (block 195), the decrease in exercise tolerance and the time span over which it occurs are logged in the combined measures set 95 (block 196).

(10) Respiratory distress quality of life (QOL) measures (block 197): If the respiratory distress QOL measure has deteriorated by more than 1.0 SD from the mean respiratory distress QOL measure in the reference baseline 26 (block 198), the increase in respiratory distress and the time span over which it occurs are logged in the combined measures set 95 (block 199).

(11) Atrial fibrillation (block 200): The presence or absence of atrial fibrillation (AF) is determined and, if present (block 201), atrial fibrillation is logged (block 202).

(12) Rhythm changes (block 203): The type and sequence of rhythm changes is significant and is determined based on the timing of the relevant rhythm measure, such as sinus rhythm. For instance, a finding that a rhythm change to atrial fibrillation precipitated circulatory measures changes can indicate therapy directions against atrial fibrillation rather than primary progression of atrial fibrillation. Thus, if there are rhythm changes (block 204), the sequence of the rhythm changes and time span are logged (block 205).

Note also that an inversion of the indicator thresholds 129 defined above could similarly be used for detecting a trend in disease regression. One skilled in the art would recognize that these measures would vary based on whether or not they were recorded during rest or during activity and that the measured activity score can be used to indicate the degree of patient rest or activity. The patient activity score can be determined via an implantable motion detector, for example, as described in U.S. Pat. No. 4,428,378, issued Jan. 31, 1984, to Anderson et al., the disclosure of which is incorporated herein by reference.

Figure 12A:
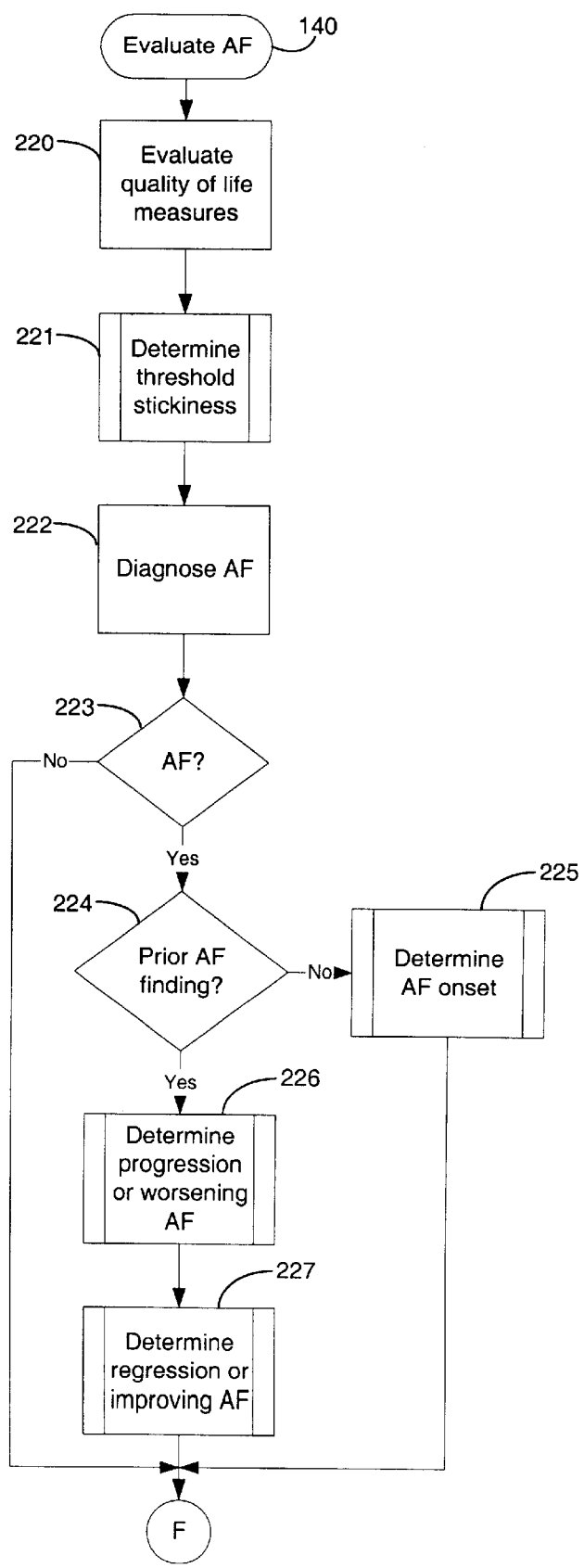
FIGS. 12A–12B are flow diagrams showing the routine for evaluating the consequences of the onset, progression, regression, and status quo associated with atrial fibrillation for use in the method of FIGS. 8A–8B.
Figure 12B:
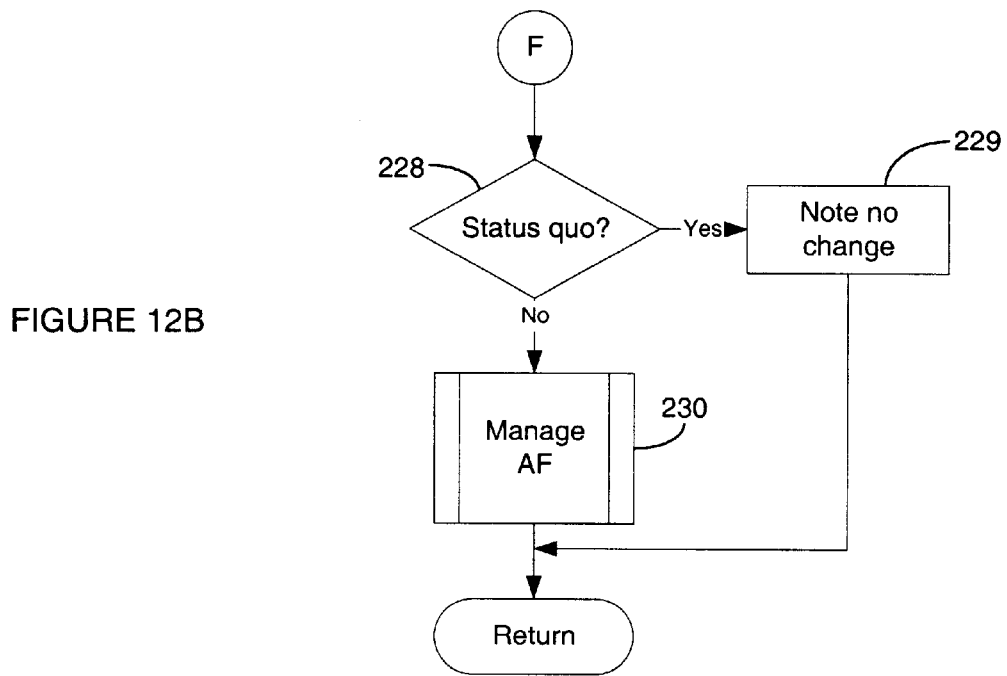

FIGS. 12A–12B are flow diagrams showing the routine for evaluating the onset, progression, regression and status quo of atrial fibrillation 140 for use in the method of FIGS. 8A and 8B. The purpose of this routine is to evaluate the presence of sufficient indicia to warrant a diagnosis of the onset, progression, regression, and status quo of atrial fibrillation and the consequential changes, if any, of comorbid disorders. Quality of life and symptom measures set 25 can be included in the evaluation (block 220) by determining whether any of the individual quality of life and symptom measures set 25 have changed relative to the previously collected quality of life and symptom measures from the monitoring sets 27 and the reference baseline 26, if used. For example, a deterioration in the shortness of breath measure 87 and exercise tolerance measure 89 would corroborate a finding of atrial fibrillation exacerbating cardiovascular or cardiopulmonary measures. Similarly, a transition from NYHA Class II to NYHA Class III would indicate a deterioration or, conversely, a transition from NYHA Class III to NYHA Class II status would indicate improvement or progress. Incorporating the quality of life and symptom measures set 25 into the evaluation can help, in part, to refute or support findings based on physiological data. Next, a determination as to whether any changes to interventive measures are appropriate based on threshold stickiness ("hysteresis") is made (block 221), as further described below with reference to FIG. 16.

The routine returns upon either the determination of a finding or elimination of all factors as follows. A diagnosis of atrial fibrillation is made (block 222) via one of many methods known in the art through the implantable medical device 12 and, in a more limited fashion, via the external medical device 26, such as described in U.S. Pat. No. 5,931,857 ('857) to Prieve et al. and U.S. Pat. No. 5,855,593 ('593) to Olson et al, the disclosures of which are incorporated herein by reference. If atrial fibrillation has occurred (block 223), the findings are categorized into reduced exercise capacity-, respiratory distress-palpitations-, and syncope-/near syncope-related atrial fibrillation as follows. First, if a finding of atrial fibrillation was not previously diagnosed (block 224), a determination categorizing disease onset is made (block 225), as further described below with reference to FIGS. 13A–13B. Otherwise, if atrial fibrillation was previously diagnosed (block 224), a further determination categorizing either disease progression (block 226) or regression (block 227) is made, as further described below with reference to FIGS. 14A–14B and 15A–15B, respectively. If, upon evaluation, neither disease onset (block 225), progression (block 226) or regression (block 227) is indicated, a finding of status quo is appropriate (block 228) and duly noted (block 229). Finally, if status quo does not exist, that is, atrial fibrillation has occurred, either as an initial onset, progression or regression (block 230), the occurrence is managed from the perspective of an effort to terminate atrial fibrillation and restore sinus rhythm, to decrease ventricular rate response, and/or to minimize the consequences of the presence of atrial fibrillation, e.g., provide anticoagulants to prevent a stroke and/or diuretics to reverse progression in congestive heart failure (block 230), as further described below with reference to FIGS. 17A–17B. The routine then returns.

Figure 13A:
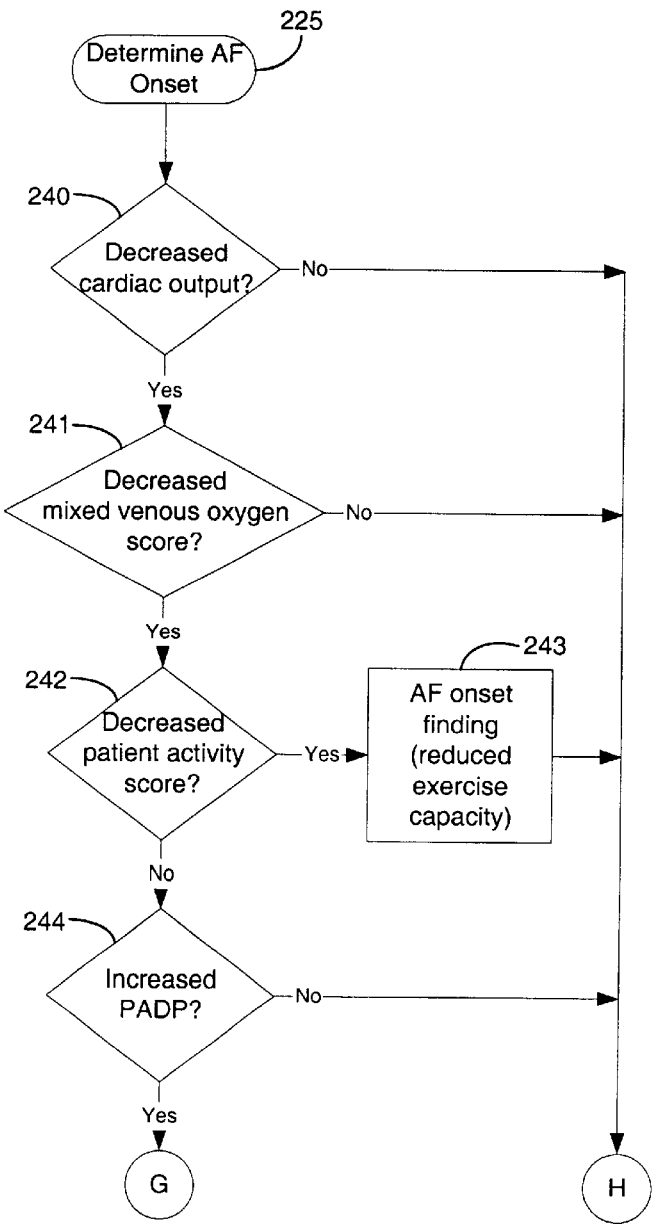
FIGS. 13A–13B are flow diagrams showing the routine for categorizing an onset of atrial fibrillation for use in the routine of FIGS. 12A–12B.
Figure 13B:
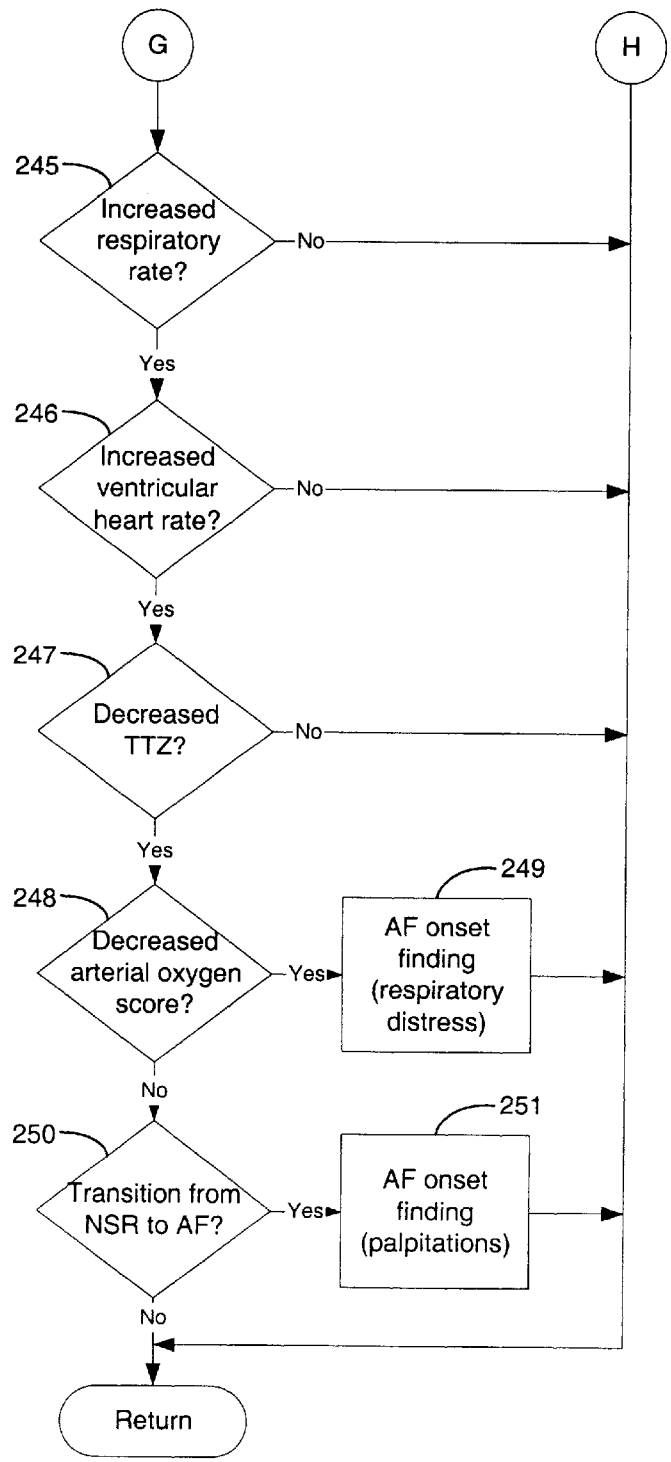

FIGS. 13A–13B are flow diagrams showing the routine for categorizing an onset of atrial fibrillation 225 for use in the routine of FIGS. 12A–12B. An effort is made to categorize atrial fibrillation manifesting primarily as resulting in reduced exercise capacity (block 243), increased respiratory distress (block 249), and/or palpitations (block 251). The clinical aspects of atrial fibrillation are described, by way of example, in E. Braunwald, ed., "Heart Disease—A Textbook of Cardiovascular Medicine," Chs. 1 and 22, W. B. Saunders Co. (1997), the disclosure of which is incorporated herein by reference.

In the described embodiment, the reduced exercise capacity, respiratory distress, and palpitations findings (blocks 243, 249, 251) can be established by consolidating the individual indications (blocks 240–242, 244–248, 250) in several ways. First, in a preferred embodiment, each individual indication (blocks 240–242, 244–248, 250) is assigned a scaled index value correlating with the relative severity of the indication. For example, decreased cardiac output (block 240) could be measured on a scale from '1' to '5' wherein a score of '1' indicates no change in cardiac output from the reference point, a score of '2' indicates a change exceeding 0.5 SD, a score of '3' indicates a change exceeding 1.0 SD, a score of '4' indicates a change exceeding 2.0 SD, and a score of '5' indicates a change exceeding 3.0 SD. The index value for each of the individual indications (blocks 240–242, 244–248, 250) can then either be aggregated or averaged with a result exceeding the aggregate or average maximum indicating an appropriate atrial fibrillation finding.

Preferably, all scores are weighted depending upon the assignments made from the measures in the reference baseline 26. For instance, arterial partial pressure of oxygen 102 could be weighted more importantly than respiratory rate 104 if the respiratory rate in the reference baseline 26 is particularly high at the outset, making the detection of further disease progression from increases in respiratory rate, less sensitive. In the described embodiment, cardiac output receives the most weight in determining a reduced exercise capacity finding, pulmonary artery diastolic pressure receives the most weight in determining a respiratory distress or dyspnea finding, and a transition from normal sinus rhythm to atrial fibrillation receives the most weight in determining a palpitations finding.

Alternatively, a simple binary decision tree can be utilized wherein each of the individual indications (blocks 240–242, 244–248, 250) is either present or is not present. Any of the individual indications (blocks 240–242, 244–248, 250) should be present for the relevant effect of atrial fibrillation on cardiovascular and cardiopulmonary measures to be affirmed as long as the atrial fibrillation is temporally related to onset.

Other forms of consolidating the individual indications (blocks 240–242, 244–248, 250) are feasible.

Figure 14A:
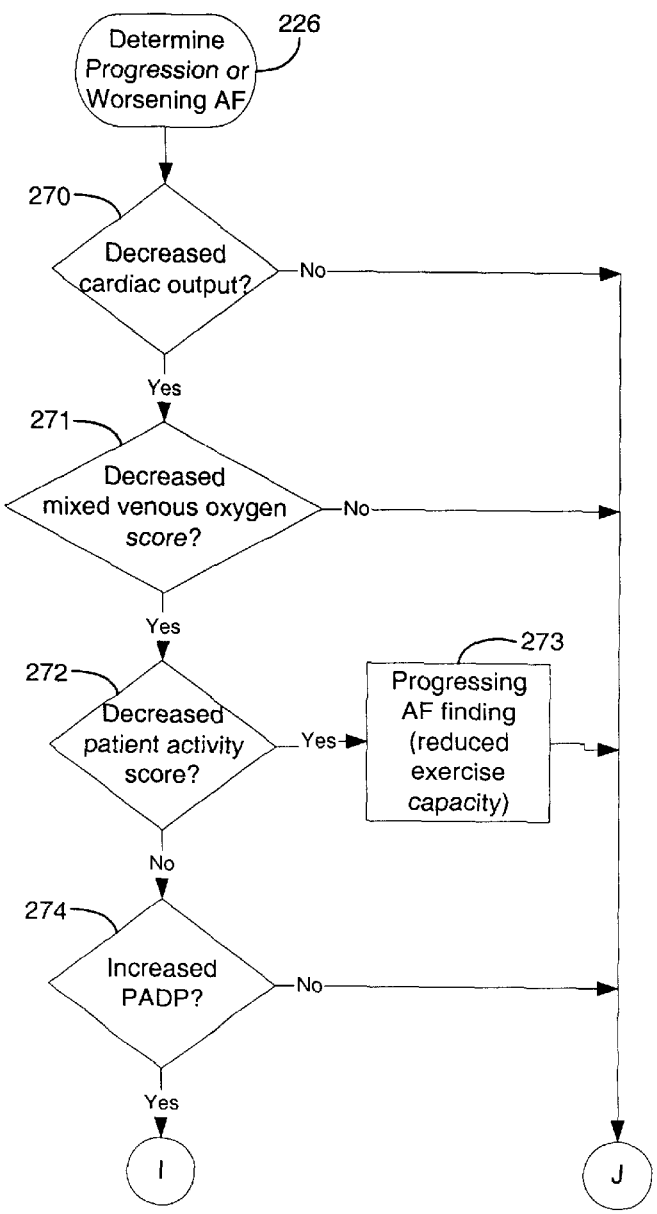
FIGS. 14A–14B are flow diagrams showing the routine for categorizing a progression or worsening of atrial fibrillation for use in the routine of FIGS. 12A–12B.
Figure 14B:
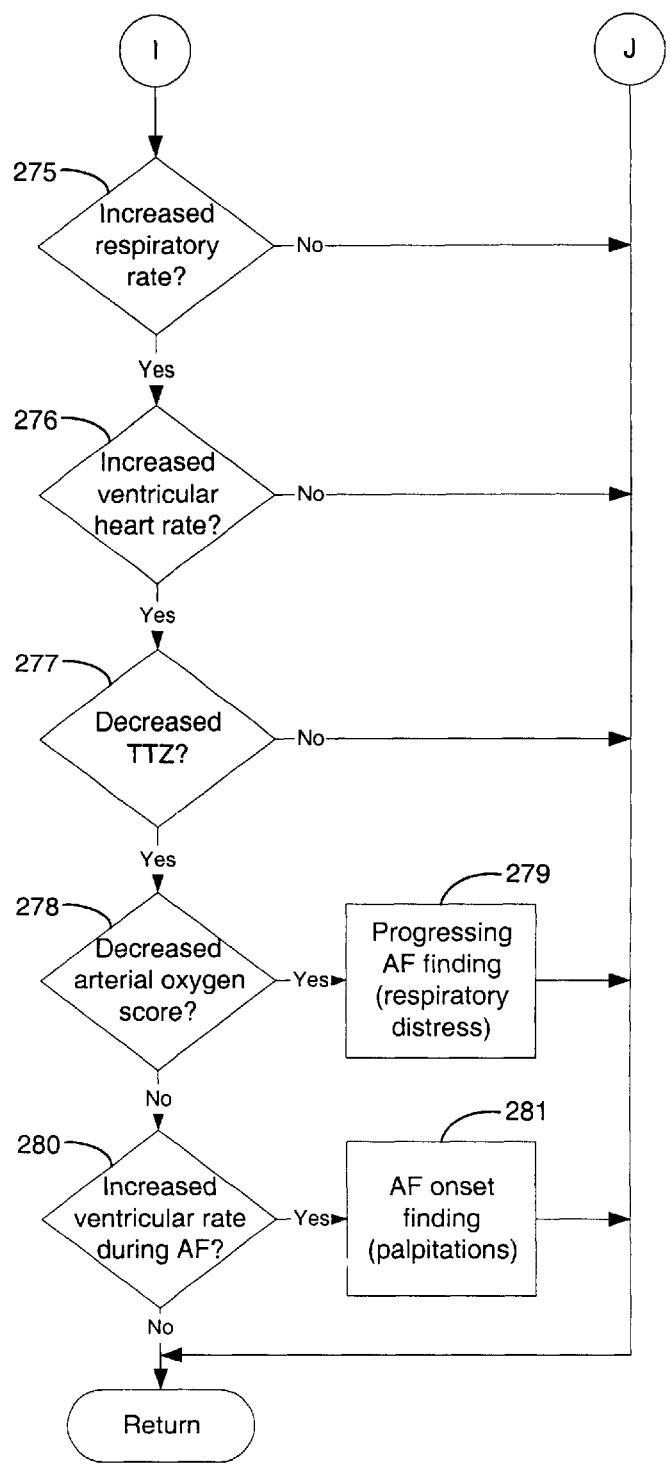

FIGS. 14A–14B are flow diagrams showing the routine for categorizing a progression or worsening of atrial fibrillation 226 for use in the routine of FIGS. 12A–12B. The primary difference between the determinations of disease onset, as described with reference to FIGS. 13A–13B, and disease progression is a demonstration of an increased ventricular rate response in atrial fibrillation or deterioration in cardiovascular or cardiopulmonary measures regardless of ventricular rate during atrial fibrillation. Whereas, to define atrial fibrillation onset, the heart rhythm must transition from normal sinus rhythm (or any non-atrial fibrillation rhythm) to atrial fibrillation as detected by any of the methods known in the art for heart rhythm diagnosis. Thus, a revised atrial fibrillation finding is possible based on the same three general symptom categories: reduced exercise capacity (block 273), respiratory distress (block 279), and palpitations (block 281). The same factors which need be indicated to warrant a diagnosis of atrial fibrillation onset and its consequences are also evaluated to determine disease progression.

Figure 15A:
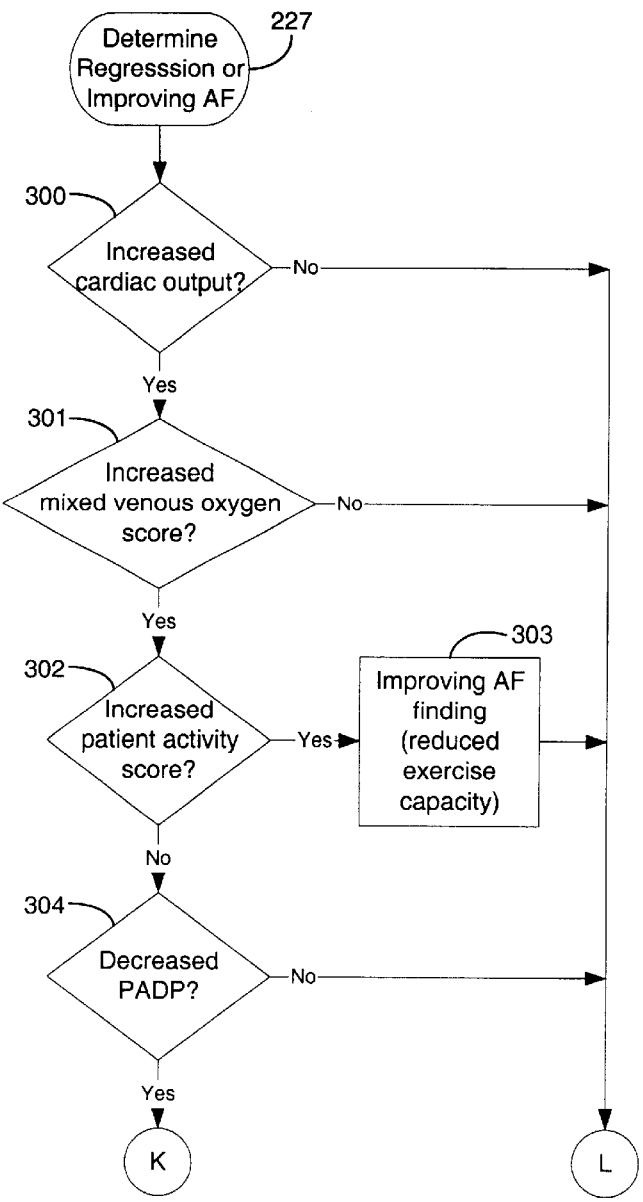
FIGS. 15A–15B are flow diagrams showing the routine for categorizing a regression or improving of atrial fibrillation 227 and its cardiovascular and cardiopulmonary consequences for use in the routine of FIGS. 12A–12B.
Figure 15B:
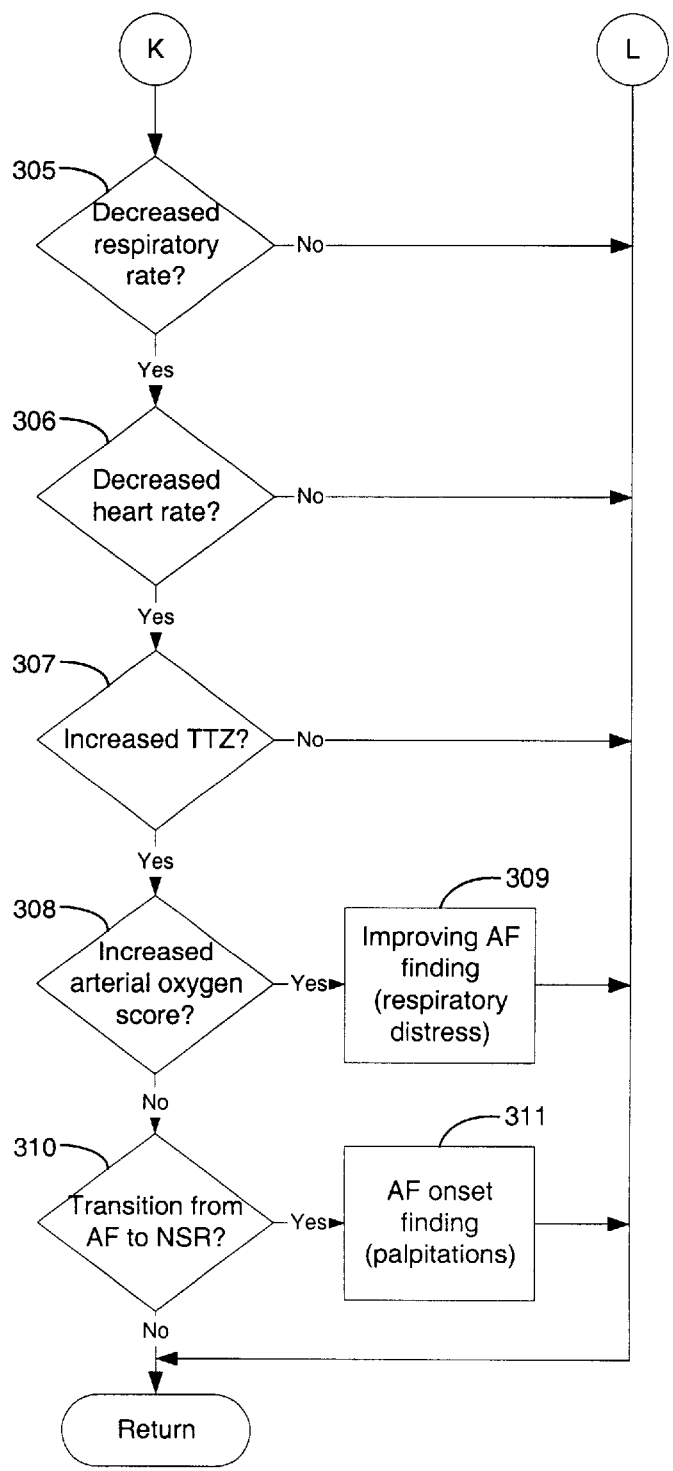

Similarly, FIGS. 15A–15B are flow diagrams showing the routine for categorizing a regression or improving of atrial fibrillation 227 and its cardiovascular and cardiopulmonary consequences for use in the routine of FIGS. 12A–12B. The same factors as described above with reference to FIGS. 13A–13B and 14A–14B, trending in opposite directions from disease onset or progression, are evaluated to determine disease regression. As primary cardiac disease considerations, multiple individual indications (blocks 300–302, 304–308, 310) should be present for the three principal findings of atrial fibrillation related reduced exercise capacity (block 303), atrial fibrillation related respiratory distress (block 309), and palpitations (block 311), to indicate disease regression.

Figure 16:
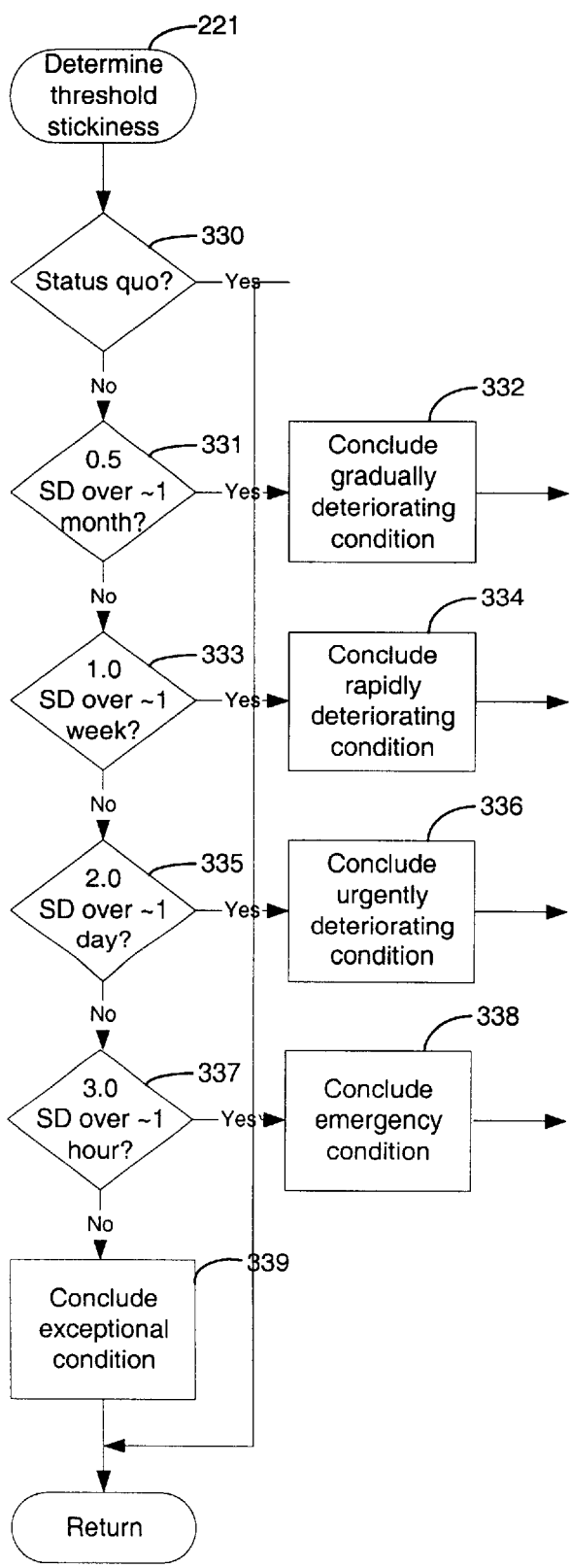
FIG. 16 is a flow diagram showing the routine for determining threshold stickiness ("hysteresis") for use in the method of FIGS. 12A–12B.

FIG. 16 is a flow diagram showing the routine for determining threshold stickiness ("hysteresis") 221 for use in the method of FIGS. 12A–12B. Stickiness, also known as hysteresis, is a medical practice doctrine whereby a diagnosis or therapy will not be changed based upon small or temporary changes in a patient reading, even though those changes might temporarily move into a new zone of concern. For example, if a patient measure can vary along a scale of '1' to '10' with '10' being worse, a transient reading of '6,' standing alone, on a patient who has consistently indicated a reading of '5' for weeks will not warrant a change in diagnosis without a definitive prolonged deterioration first being indicated. Stickiness dictates that small or temporary changes in cardiovascular or cardiopulmonary physiology associated with atrial fibrillation onset, progression or regression require more diagnostic certainty, as confirmed by the persistence of the changes, than large changes would require for any of the monitored (device) measures. Stickiness also makes reversal of important diagnostic decisions, particularly those regarding life-threatening disorders, more difficult than reversal of diagnoses of modest import. As an example, automatic external defibrillators (AEDs) manufactured by Heartstream, a subsidiary of Agilent Technologies, Seattle, Washington, monitor heart rhythms and provide interventive shock treatment for the diagnosis of ventricular fibrillation. Once diagnosis of ventricular fibrillation and a decision to shock the patient has been made, a pattern of no ventricular fibrillation must be indicated for a relatively prolonged period before the AED changes to a "no-shock" decision. As implemented in this AED example, stickiness mandates certainty before a decision to shock is disregarded.

In practice, stickiness also dictates that acute deteriorations in disease state are treated aggressively while chronic, more slowly progressing disease states are treated in a more tempered fashion. Thus, if the patient status indicates a status quo (block 330), no changes in treatment or diagnosis are indicated and the routine returns. Otherwise, if the patient status indicates a change away from status quo (block 330), the relative quantum of change and the length of time over which the change has occurred is determinative. If the change of approximately 0.5 SD has occurred over the course of about one month (block 331), a gradually deteriorating condition exists (block 332) and a very tempered diagnostic, and if appropriate, treatment program is undertaken. If the change of approximately 1.0 SD has occurred over the course of about one week (block 333), a more rapidly deteriorating condition exists (block 334) and a slightly more aggressive diagnostic, and if appropriate, treatment program is undertaken. If the change of approximately 2.0 SD has occurred over the course of about one day (block 335), an urgently deteriorating condition exists (block 336) and a moderately aggressive diagnostic, and if appropriate, treatment program is undertaken. If the change of approximately 3.0 SD has occurred over the course of about one hour (block 337), an emergency condition exists (block 338) and an immediate diagnostic, and if appropriate, treatment program is undertaken as is practical. Finally, if the change and duration fall outside the aforementioned ranges (blocks 331–338), an exceptional condition exists (block 339) and the changes are reviewed manually, if necessary. The routine then returns. These threshold limits and time ranges may then be adapted depending upon patient history and peer-group guidelines.

The form of the revised treatment program depends on the extent to which the time span between changes in the device measures exceed the threshold stickiness 133 (shown in FIG. 5) relating to that particular type of device measure. For example, threshold stickiness 133 indicator for monitoring a change in heart rate in a chronic patient suffering from atrial fibrillation might be 10% over a week. Consequently, a change in average heart rate 96 (shown in FIG. 4) from 80 bpm to 95 bpm over a seven day period, where a 14 beat per minute average change would equate to a 1.0 SD change, would exceed the threshold stickiness 133 and would warrant a revised medical diagnosis perhaps of disease progression. One skilled in the art would recognize the indications of acute versus chronic disorders which will vary upon the type of disease, patient health status, disease indicators, length of illness, and timing of previously undertaken interventive measures, plus other factors.

Figure 17A:
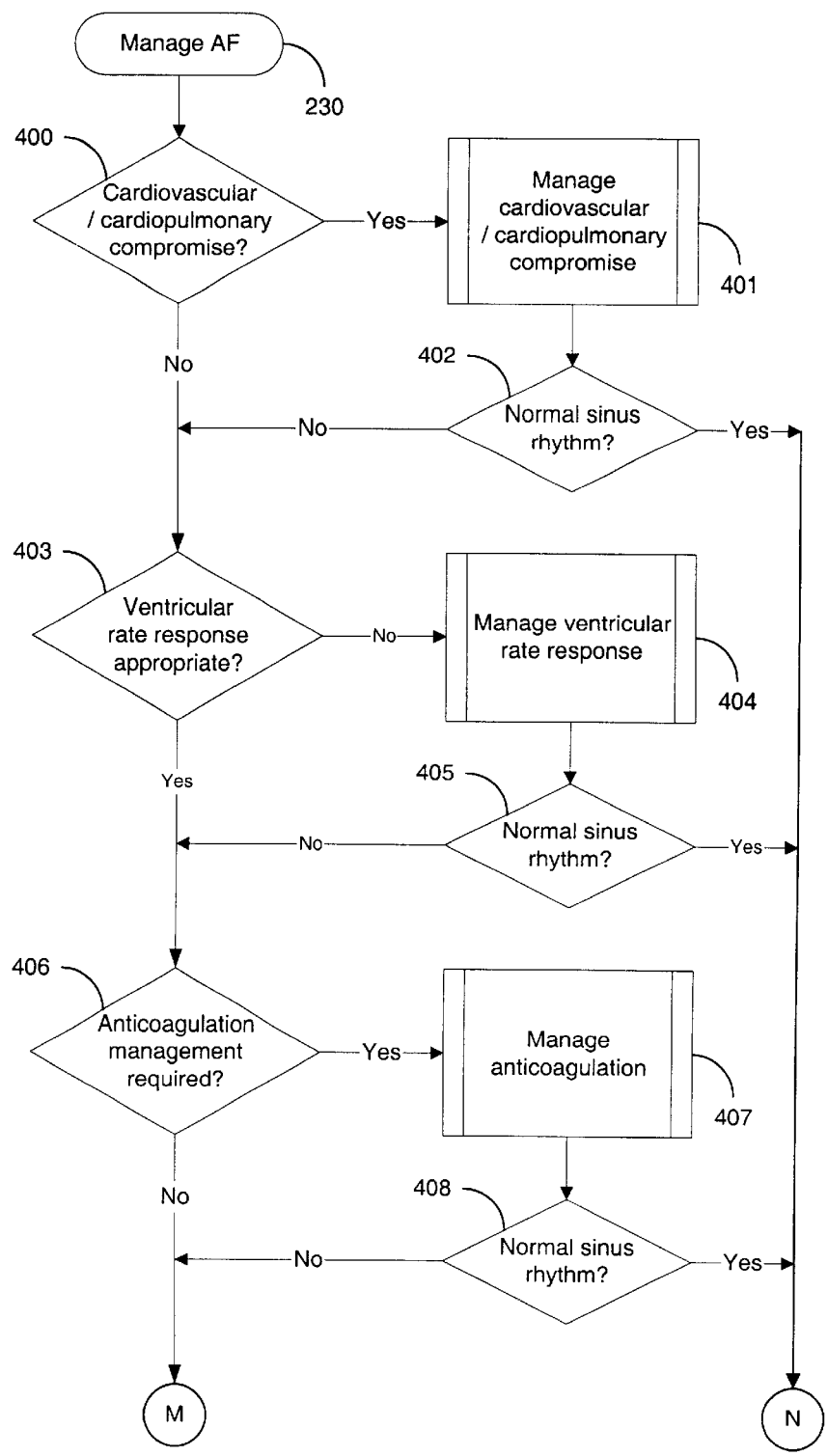
FIGS. 17A–17B is a flow diagram showing the routine for managing the consequences of atrial fibrillation for use in the routine of FIGS. 12A–12B.
Figure 17B:
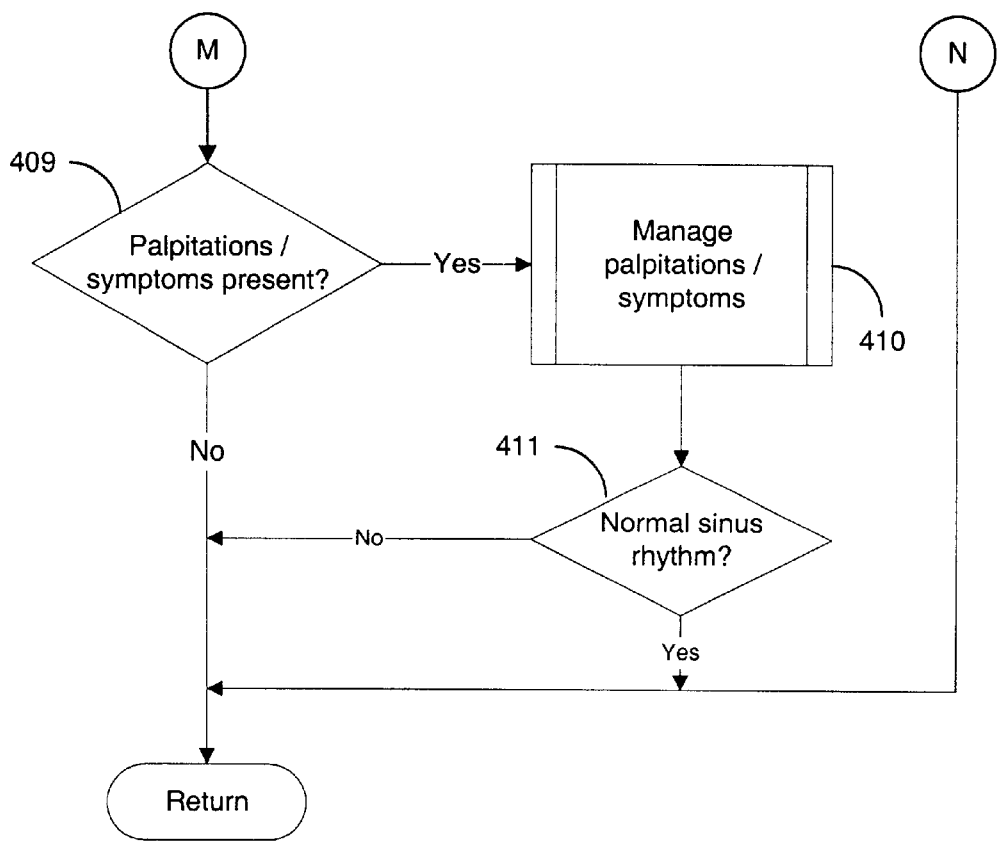
Figure 18A:
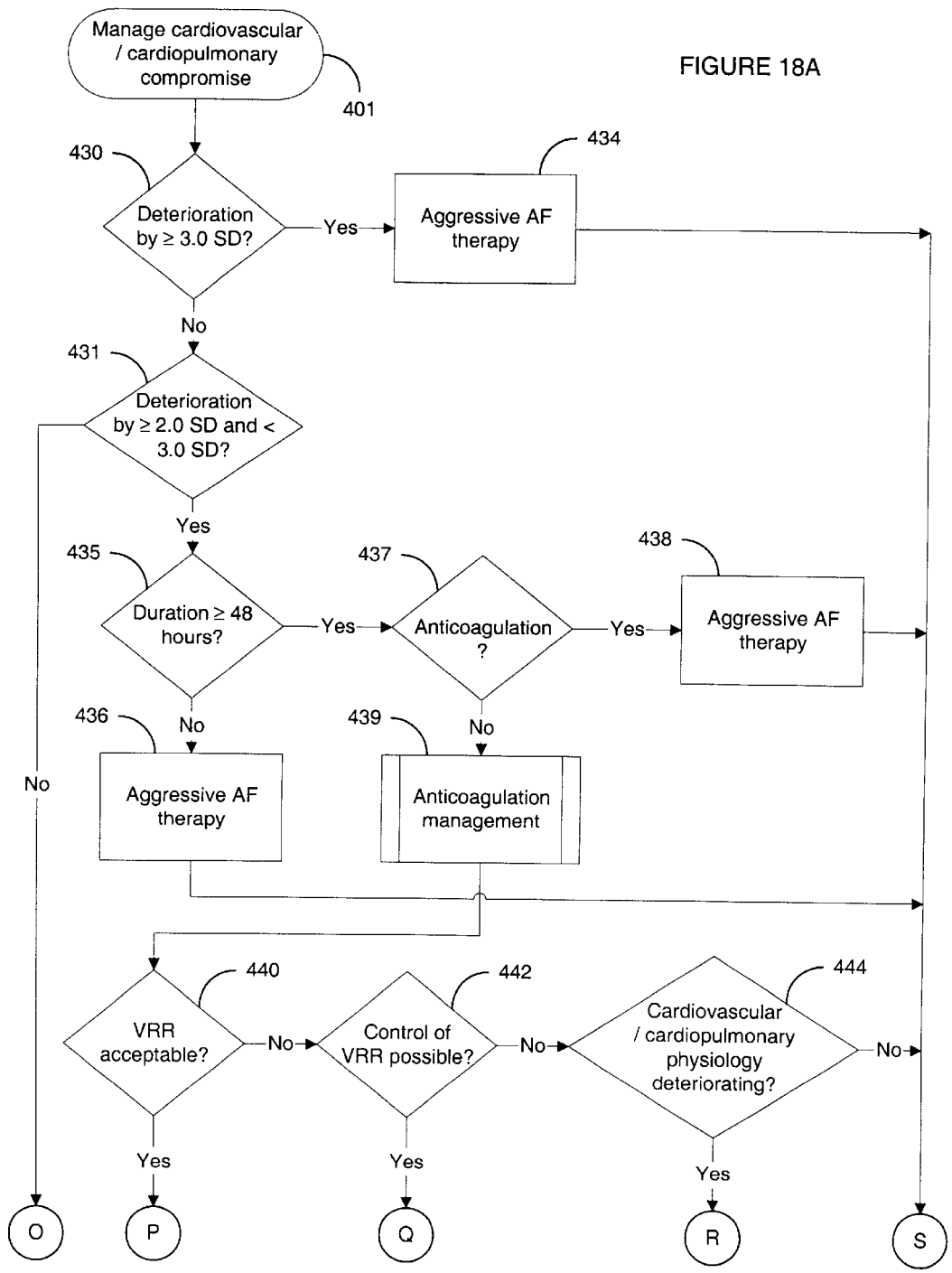
FIGS. 18A–18D are flow diagrams showing the routine for managing a cardiovascular/cardiopulmonary compromise for use in the method of FIGS. 17A–17B.
Figure 18B:
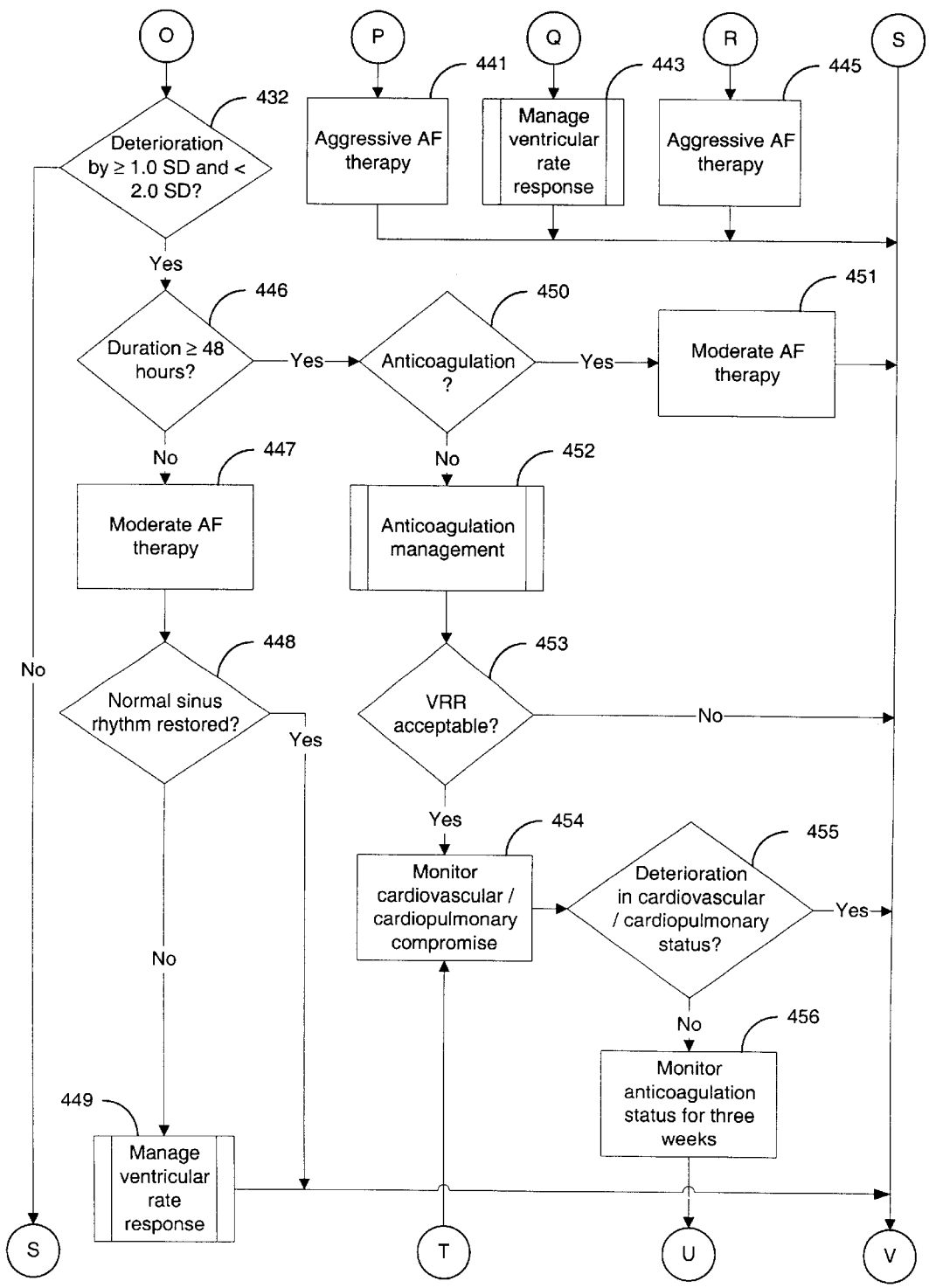
Figure 18C:
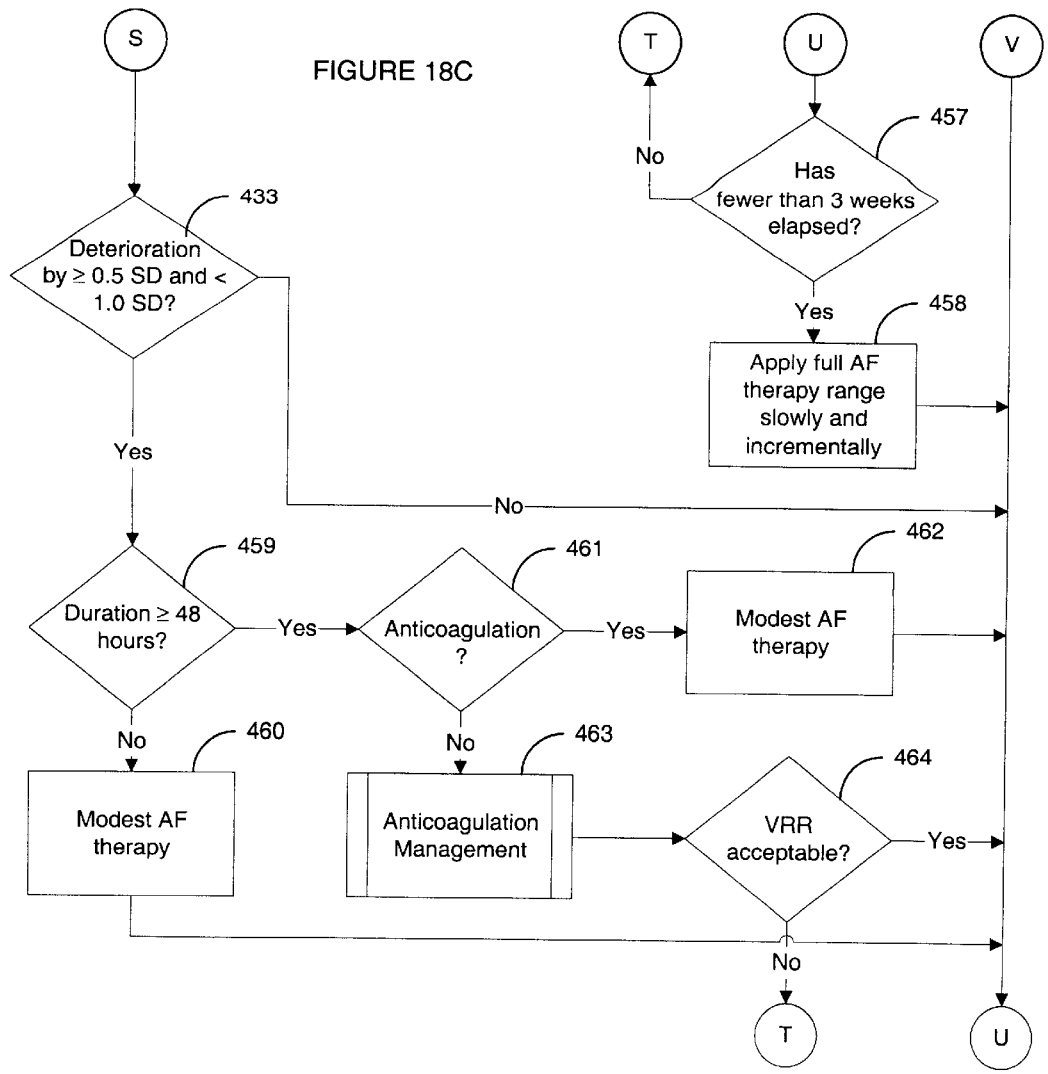
Figure 18D:
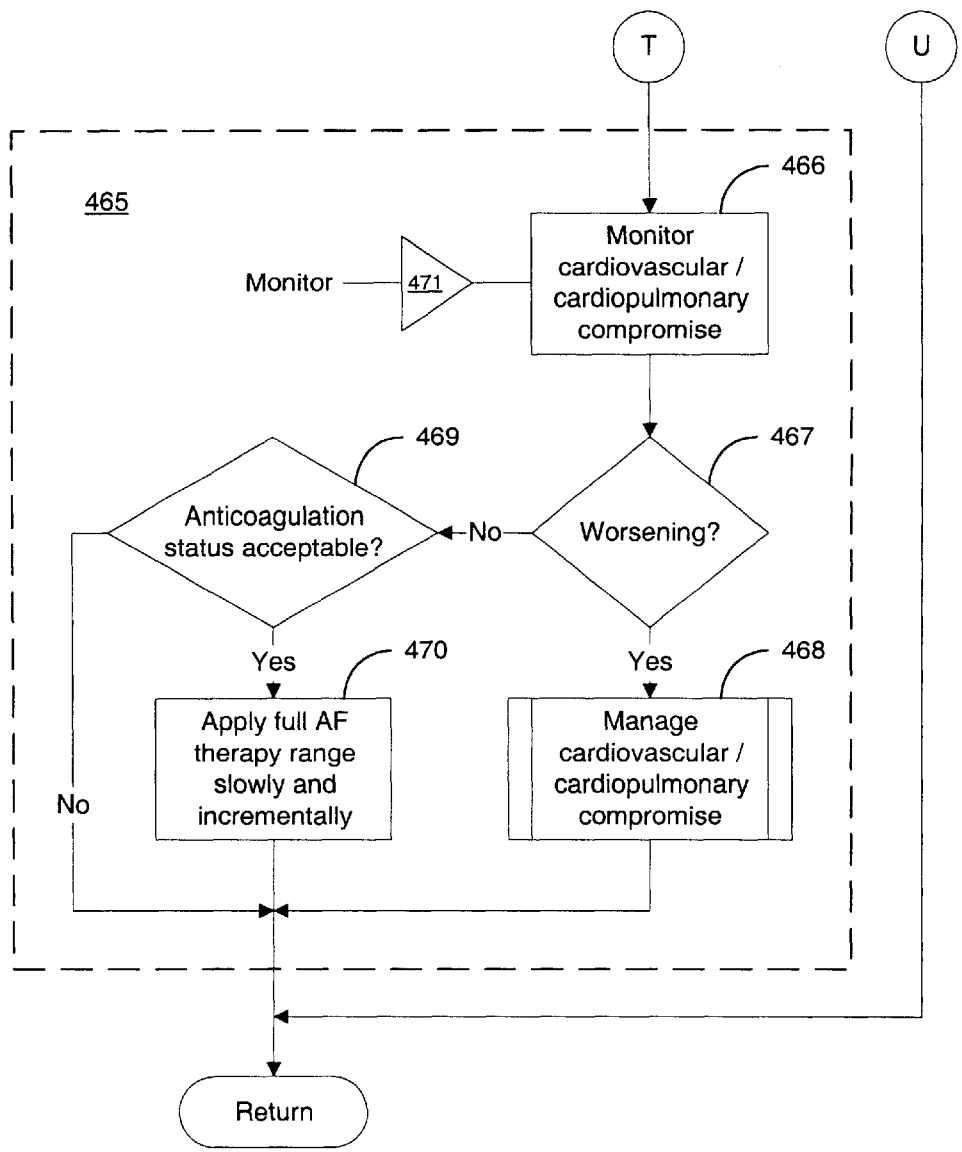

FIGS. 17A–17B is a flow diagram showing the routine for managing the consequences of atrial fibrillation 230 for use in the routine of FIGS. 12A–12B. The management of atrial fibrillation focuses principally on restoring normal sinus rhythm and controlling ventricular rate response (VRR). However, effective atrial fibrillation management requires considering four individual areas of concern: cardiovascular/cardiopulmonary compromise, ventricular rate response, anticoagulation status, and associated symptoms, like the presence of palpitations. An overriding theme is that restoration of normal sinus rhythm should not be attempted for atrial fibrillation greater than or equal to 48 hours in duration in the absence of anticoagulation or serious cardiovascular/cardiopulmonary compromise to prevent stroke. Consequently, therapy should usually be directed to control of ventricular rate response under such circumstances.

Each of these areas of concern may potentially overlap and require coordinated therapeutic treatment. The management process that follows, although outlined in linear, sequential fashion, can be performed in a simultaneous manner, where clinically reasonable and necessary. One concern of persistent atrial fibrillation is a time-based threat of thromboembolic disease if atrial fibrillation persists for longer than 48 hours and the patient's blood is not anticoagulated. Atrial fibrillation should, if possible and clinically reasonable, be terminated if atrial fibrillation reaches a duration exceeding 48 hours. In addition, atrial fibrillation of any duration may be accompanied by cardiovascular decompensation, including a decrease in cardiac output, an increase in cardiac filling pressures, a decrease in blood pressure, a decrease in oxygenation, and an increase in myocardial ischemia, particularly if atrial fibrillation presents in conjunction with comorbid disorders. Again, if possible and clinically reasonable, atrial fibrillation should be terminated. Although atrial fibrillation may, in and of itself, affect cardiovascular physiology adversely, a component of the response may be due to a ventricular rate response which is either too rapid or too slow. Thus, control of ventricular rate response constitutes a third management concern. Palpitations are caused by an irregular heartbeat which, while possibly uncomfortable to a patient, usually need only be monitored and not treated. In the event of disabling palpitations, or other related symptoms such as dyspnea or fatigue, however, atrial fibrillation can be electrically or pharmacologically terminated.

The four areas of concern regarding atrial fibrillation management are addressed as follows. First, if a cardiovascular/cardiopulmonary compromise exists (block 400), the compromise must be actively managed (block 401), as further described below with reference to FIGS. 18A–18D. After the completion of cardiovascular/cardiopulmonary compromise management (block 401), if normal sinus rhythm has been restored (block 402), the routine returns. If ventricular rate response is inappropriate, that is, either too rapid or too slow (block 403), ventricular rate response must be actively managed (block 404), as further described below with reference to FIG. 19. After the completion of ventricular rate response management (block 404), if ventricular rate response has been controlled (block 405), the routine returns. If anticoagulation management is required (block 406), such management is undertaken (block 407), as further described below with reference to FIG. 20. After the completion of anticoagulation management (block 407), if normal sinus rhythm has been restored (block 408), the routine returns. Otherwise, if palpitations/symptoms are present (block 409), the palpitations/symptoms are actively managed (block 410), as further described below with reference to FIG. 21. After the completion of palpitations/symptoms management (block 410), if normal sinus rhythm has been restored (block 411), the routine returns. Finally, if none of cardiovascular/cardiopulmonary compromise (block 400), inappropriate ventricular rate response (block 403), anticoagulation management (block 406), or palpitations/symptoms (block 409) are presented, no further action is taken and the routine returns.

FIGS. 18A–18D are flow diagrams showing the routine for managing a cardiovascular/cardiopulmonary compromise 401 for use in the method of FIGS. 17A–17B. The purpose of this routine is to determine an appropriate treatment regimen for a cardiovascular/cardiopulmonary compromise by classifying the relative magnitude of change in physiological measures obtained or derived from the device and derived measures sets 24a, 24b (shown in FIG. 1) into ranges of severity. The degree of medical intervention varies proportionate to the severity, magnitude of change and the time span over which the change occurred. Thus, deterioration greater than or equal to 3.0 SD (block 430) requires immediate, aggressive therapy regardless of anticoagulation status, whereas deterioration greater than or equal to than 0.5 SD but less than 1.0 SD (block 433) may require only modest therapy.

Beginning with maximum change, if the deterioration in physiological measures is greater than or equal to 3.0 SD (block 430), aggressive atrial fibrillation therapy, as defined below, is undertaken (block 434). Otherwise, if the deterioration in physiological measures is greater than or equal to 2.0 SD but less than 3.0 SD (block 431), the duration of atrial fibrillation and usage of anticoagulation drug therapy is considered. Thus, if atrial fibrillation has lasted fewer than 48 hours (block 435) or if at least 48 hours or longer and with anticoagulation therapy (block 437), aggressive atrial fibrillation therapy is undertaken (blocks 436, 438, respectively). Otherwise, if atrial fibrillation has lasted at least 48 hours or longer (block 435) but without anticoagulation therapy (block 437), anticoagulation management is undertaken (block 439), as further described below with reference to FIG. 20.

Upon completion of anticoagulation management (block 435), a ventricular rate response analysis (blocks 440–444) is performed as follows. First, if ventricular rate response is acceptable (block 440), aggressive atrial fibrillation therapy is undertaken (block 441). Otherwise, if ventricular rate response in not acceptable (block 440) and control of ventricular rate response is possible (block 442), ventricular rate response management is undertaken (block 443), as further described below with reference to FIG. 19. Conversely, if ventricular rate response is not acceptable (block 442), control of ventricular rate response is not possible (block 442), and cardiovascular/cardiopulmonary physiology is deteriorating (block 444), aggressive atrial fibrillation therapy is undertaken (block 445).

On the lower range of change in physiological measures, if the deterioration in physiological measures is greater than 1.0 SD but less than 2.0 SD (block 432), the duration of atrial fibrillation and usage of anticoagulation drug therapy is considered. Thus, if atrial fibrillation has lasted fewer than 48 hours (block 446), moderate atrial fibrillation therapy, as defined below, is undertaken (block 447). If normal sinus rhythm has been restored (block 448), no further action is required. Otherwise, ventricular rate response management is (block 449), as further described below with reference to FIG. 19. If atrial fibrillation has lasted at least 48 hours or longer (block 446), the administration of anticoagulation drug therapy is considered. If anticoagulation drug therapy has already been undertaken (block 450), moderate atrial fibrillation therapy is undertaken (block 451). Otherwise, anticoagulation management is undertaken (block 452), as further described below with reference to FIG. 20.

Upon completion of anticoagulation management (block 452), a ventricular rate response analysis (blocks 453–458) is performed during atrial fibrillation as follows. First, if ventricular rate response is acceptable (block 453), cardiovascular/cardiopulmonary compromise is monitored (block 454). If the cardiovascular/cardiopulmonary status shows deterioration (block 455), the anticoagulation status is monitored (block 456) and, if fewer than three weeks have elapsed (block 457), therapy is dictated by cardiovascular/cardiopulmonary status (block 454). Otherwise, if appropriate anticoagulation drug therapy has continued for at least three weeks with no substantial change in cardiovascular/cardiopulmonary compromise status (block 455), the full range of atrial fibrillation therapies are slowly and incrementally applied, that is, from modest to moderate to aggressive, as is reasonably necessary and matched to the patient's condition (block 458).

Finally, if the deterioration in physiological measures at the onset of atrial fibrillation is greater than 0.5 SD but less than 1.0 SD (block 433), the duration of atrial fibrillation and usage of anticoagulation drug therapy is again considered. Thus, if atrial fibrillation has lasted fewer than 48 hours (block 459), modest atrial fibrillation therapy, as defined below, is undertaken (block 460). However, if atrial fibrillation has lasted at least 48 hours or longer (block 459), the administration of anticoagulation drug therapy is considered. If anticoagulation drug therapy has already been undertaken (block 461), modest atrial fibrillation therapy is undertaken (block 462). Otherwise, anticoagulation management is undertaken (block 463), as further described below with reference to FIG. 20.

Upon completion of anticoagulation management (block 463), a ventricular rate response analysis (blocks 464–470) is performed as follows. First, if ventricular rate response is acceptable (block 464), no further action is taken. Otherwise, cardiovascular/cardiopulmonary compromise is monitored (block 466) using a standard cardiovascular/cardiopulmonary monitoring procedure (box 465). If the cardiovascular/cardiopulmonary status shows a worsening of the atrial fibrillation condition (block 467), the compromise is managed (block 468) by recursively performing the present routine. Otherwise, if the condition is improving (or maintaining status quo) (block 467) and the anticoagulation drug therapy status is acceptable (block 469), the full range of atrial fibrillation therapies are slowly and incrementally applied, that is, from modest to moderate to aggressive, as is reasonably necessary and matched to the patient's condition (block 470). The routine then returns.

Note if the deterioration in physiological measures is less than 0.5 SD (block 433), no action is taken unless dictated by cardiovascular/cardiopulmonary measures.

Figure 19:
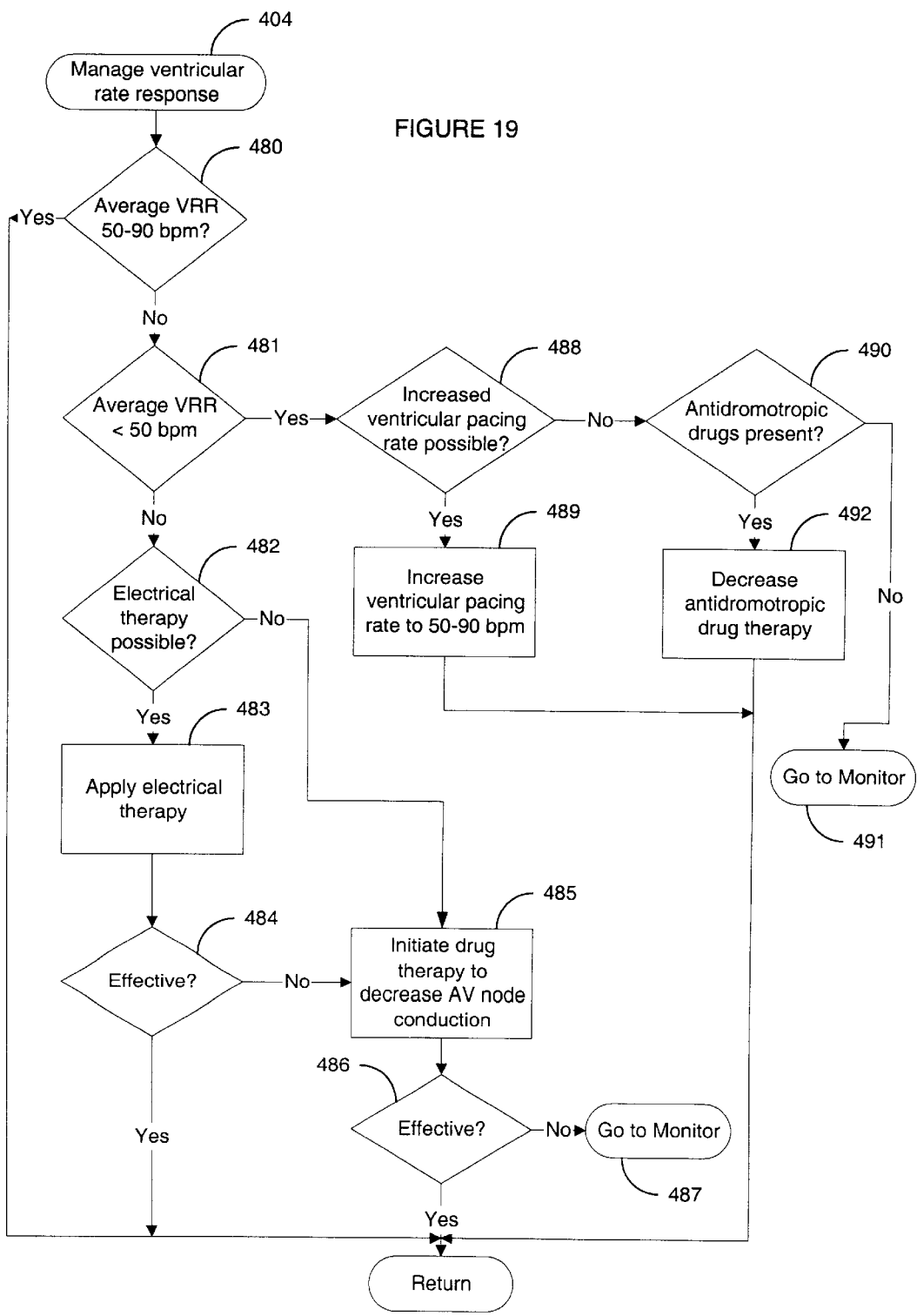
FIG. 19 is a flow diagram showing the routine for managing ventricular rate response for use in the method of FIGS. 17A–17B.

FIG. 19 is a flow diagram showing the routine for managing ventricular rate response 404 for use in the method of FIGS. 17A–17B. The purpose of this routine is to bring ventricular rate response into a 50–90 beats per minute (bpm) average range. Thus, if the average ventricular rate response is within a "good" range of 50–90 bpm (block 480), no further action need be taken and the routine returns. Otherwise, if the average ventricular rate response is not less than 50 bpm, that is, in excess of 90 bpm and thence too fast (block 481), actions to decrease the ventricular pacing rate are considered. First, electrical therapy is undertaken (block 483) if such therapy is possible (block 482), such as described in U.S. Pat. No. 5,356,425 to Bardy et al., the disclosure of which is incorporated herein by reference. If the electrical therapy was not effective (block 484) or if electrical therapy is not possible (block 482), drug therapy to decrease atrioventricular (AV) node conduction is undertaken (block 485). If the drug therapy was not effective (block 486), cardiovascular/cardiopulmonary comprise is monitored (block 487) by performing the standard monitoring procedure (starting at block 471 in box 465 in FIGS. 18A–18D) where further management is dictated by the cardiovascular/cardiopulmonary measures.

If the average ventricular rate response is less than 50 bpm, that is, too slow (block 481), actions to increase the ventricular pacing rate are considered. If an increased ventricular pacing rate is possible (block 488), the ventricular pacing rate is increased, preferably to within a range of 50–90 bpm (block 489), modified by the outcome in cardiovascular/cardiopulmonary measures. Otherwise, if increased ventricular pacing is not possible (block 488) and antidromotropic drugs (drugs that slow atrioventricular node conduction) are present (block 492), the antidromotropic drug therapy is decreased (block 492). Otherwise, if antidromotropic drugs are present (block 490), cardiovascular/cardiopulmonary compromise is monitored (block 491) by performing the standard monitoring procedure (starting at block 471 in box 465 in FIGS. 18A–18D). The routine then returns.

Figure 20:
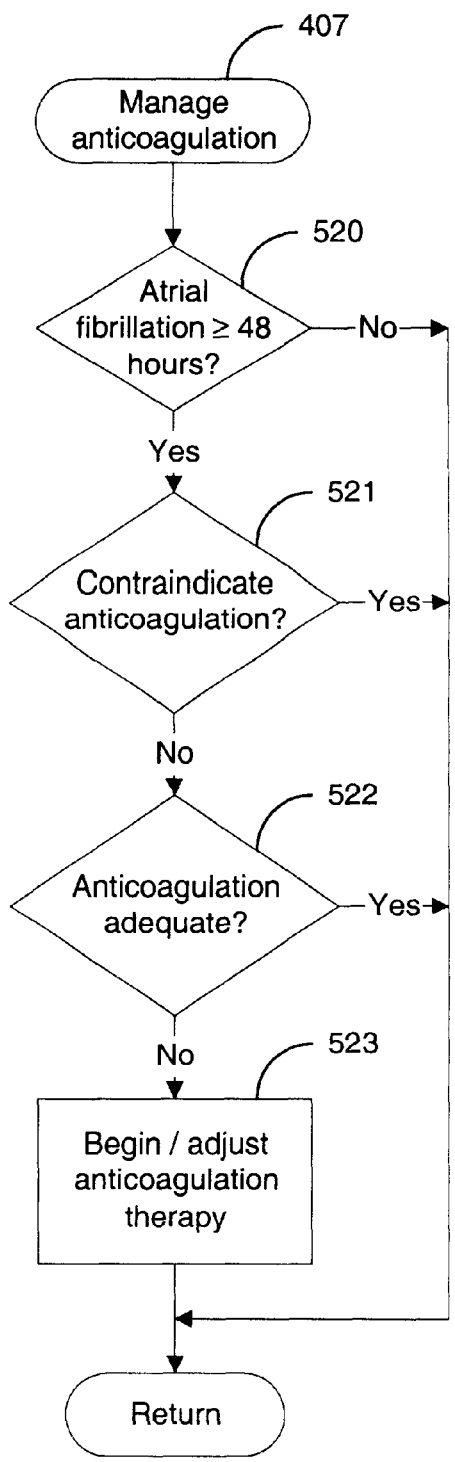
FIG. 20 is a flow diagram showing the routine for managing anticoagulation for use in the method of FIGS. 17A–17B.

FIG. 20 is a flow diagram showing the routine for managing anticoagulation 407 for use in the method of FIGS. 17A–17B. The purpose of this routine is to initiate or adjust anticoagulation drug therapy based on the duration of atrial fibrillation and anticoagulation drug therapy status. Anticoagulation drug therapy is not required if atrial fibrillation has persisted for less than 48 hours (block 520) or if the condition of the patient contraindicates such therapy (block 521). Similarly, an adjustment to existing anticoagulation drug therapy is inappropriate if the anticoagulation is already adequate (block 522). Thus, if atrial fibrillation has lasted at least 48 hours or longer (block 520), anticoagulation is not contraindicated (block 521) and any present anticoagulation drug therapy is insufficient (block 522), anticoagulation drug therapy is started or adjusted, as appropriate (block 523) to maintain an International Normalized Ratio (INR) of 2.0–3.0. The routine then returns.

Figure 21:
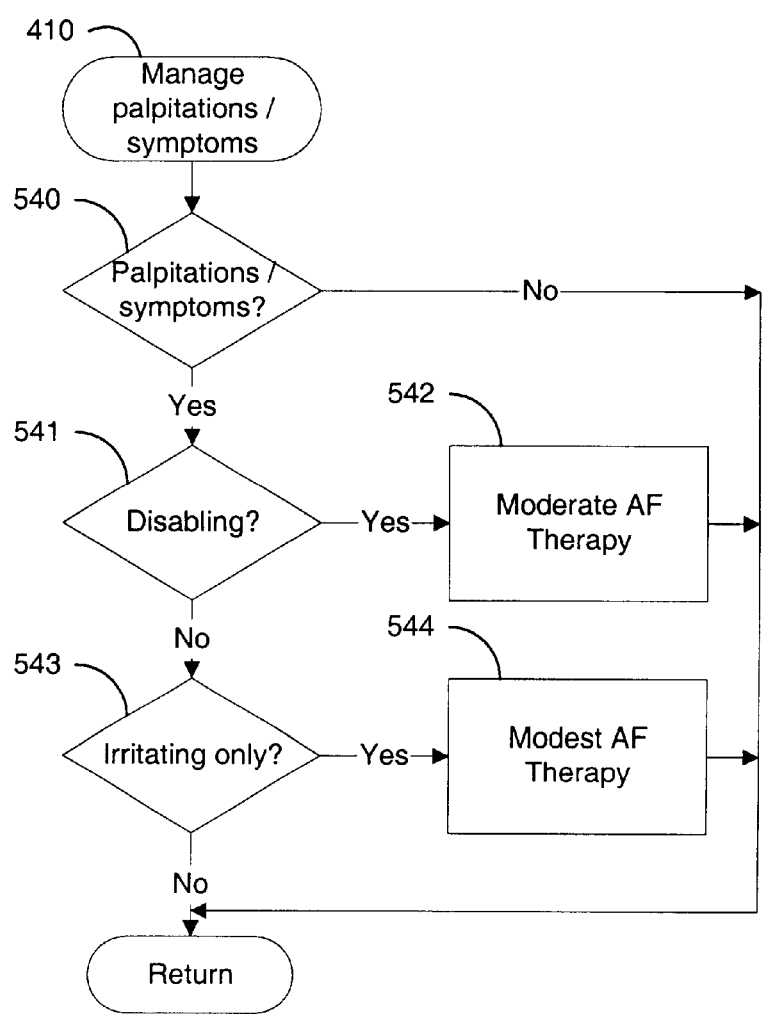
FIG. 21 is a flow diagram showing the routine for managing palpitations for use in the method of FIGS. 17A–17B.

FIG. 21 is a flow diagram showing the routine for managing palpitations/symptoms 410 for use in the method of FIGS. 17A–17B. The purpose of this routine is to determine the proper quantum of atrial fibrillation therapy for a palpitating heartbeat, fatigue, dyspnea, or related symptoms. If palpitations/symptoms are present (block 540) and disabling to the patient (block 541), moderate atrial fibrillation therapy is undertaken (block 542). However, if the palpitations/symptoms are not disabling (block 541) and are merely irritating to the patient (block 543), modest atrial fibrillation is undertaken (block 544). Finally, if the palpitations/symptoms are not disabling (block 541) nor irritating (block 543), no action is taken. The routine then returns.

A range of therapies with which to treat atrial fibrillation are available, including the following, non-exclusive exemplary list:

1. Electrical shock to restore normal sinus rhythm.
2. Antitachycardia pacing maneuvers to restore normal sinus rhythm.
3. Implantable medical device (or non-device) infusion of drugs to restore normal sinus rhythm.
4. Oral administration of drugs to restore normal sinus rhythm.
5. Electrical pacing maneuvers to decrease ventricular rate response.
6. Electrical pacing maneuvers to increase ventricular rate response.
7. Implantable medical device (or non-device) infusion of drugs to decrease ventricular rate response.
8. Implantable medical device (or non-device) infusion of drugs to increase ventricular rate response.
9. Oral administration of drugs to decrease ventricular rate response.
10. Oral administration of drugs to increase ventricular rate response.
11. Discontinuation or withdrawal of drug therapy to restore normal sinus rhythm.
12. Discontinuation or withdrawal of drug therapy to decrease ventricular rate response.
13. Discontinuation or withdrawal of drug therapy to increase ventricular rate response.

Other therapies for restoration of normal sinus rhythm or to favorably alter ventricular rate response are also feasible, as is known in the art.

The foregoing therapies can be approximately categorized into three groupings of treatments to attempt to restore normal sinus rhythm or, as appropriate, to increase or decrease ventricular rate response, as follows:

1. Aggressive Therapy (in order of preference):
    a. Apply immediate electrical shock therapy to effect termination of atrial fibrillation.
    b. If electrical shock therapy is ineffective, administer most effective drug intravenously, regardless of drug side effects.
    c. If drug thereby in isolation is ineffective, apply further electrical shock therapy in the presence of drug therapy.
2. Moderate Therapy (in order of preference):
    a. Apply time restricted electrical pacing therapies, not more than one hour in duration.
    b. If time restricted electrical pacing therapies are ineffective, administer most effective drug intravenously or by implantable medical device (or non-device), regardless of drug side effects.
    c. If time restricted electrical pacing and drug therapies are ineffective, apply electrical shock therapy.
    d. Administer oral drug therapy using agents of any potency and side effect profile.
    e. Combine oral drug therapy with electrical therapy.
3. Modest Therapy (in order of preference):
    a. Liberally apply electrical pacing therapies, not more than one day in duration.
    b. Administer oral drug therapy using agents with only modest side effects.
    c. Only with patient approval, consider electrical shock or more aggressive drug therapies.

The present invention provides several benefits. One benefit is improved predictive accuracy from the outset of patient care when a reference baseline is incorporated into the automated diagnosis and when physiological measures immediately antecedent to the onset of atrial fibrillation can be examined to gauge the likelihood of precipitating factors, like heart failure, myocardial ischemia and pulmonary insufficiency as well as more subtle measures of cardiac electrophysiology. This post-hoc analysis following each episode of atrial fibrillation onset is likely to prove particular important in patients with primary atrial fibrillation, that is those with no known associated diseases or explanations for the onset of atrial fibrillation.

A further benefit is an expanded knowledge base created by expanding the methodologies applied to a single patient to include patient peer groups and the overall patient population. Collaterally, the information maintained in the database could also be utilized for the development of further predictive techniques and for medical research purposes. Yet a further benefit is the ability to hone and improve the predictive techniques employed through a continual reassessment of patient outcomes.

Other benefits include an automated, expert system approach to the cross-referral, consideration, and potential finding or elimination of other diseases and health disorders with similar or related etiological indicators and for those other disorders that may have an impact on atrial fibrillation. Although disease specific markers will prove very useful in discriminating the underlying cause of symptoms, many diseases, other than atrial fibrillation, will alter some of the same physiological measures resulting from atrial fibrillation. Consequently, an important aspect of considering the potential impact of other disorders will be, not only the monitoring of atrial fibrillation onset and offset and the ventricular rate during atrial fibrillation, but the sequencing of change and the temporal evolution of physiological measures, for example respiratory rate, arterial oxygenation, ST segment evolution and cardiac output, to reflect the pathophysiological consequences of atrial fibrillation onset, progression or regression in other disease processes.

Finally, the benefit of this invention tempers therapy of atrial fibrillation in a measured and clinically balanced fashion comparable to the management afforded by expert human cardiac care.

While the invention has been particularly shown and described as referenced to the embodiments thereof, those skilled in the art will understand that the foregoing and other changes in form and detail may be made therein without departing from the spirit and scope of the invention.

What is claimed is:

1. An automated method for diagnosing and monitoring an outcome of atrial fibrillation, comprising:
   retrieving a plurality of monitoring sets from a database with each monitoring set comprising recorded measures relating to patient information recorded on a substantially continuous basis;
   diagnosing atrial fibrillation;
   determining a patient status change in response to the atrial fibrillation diagnosis for an absence, an onset, a progression, a regression, and a status quo of atrial fibrillation by comparing at least one of the recorded measures from each of the monitoring sets to at least one other of the recorded measures with both recorded measures relating to the same type of patient information; and
   testing the recorded measure comparison against an indicator threshold corresponding to the same type of patient information as the recorded measures which were compared to form the atrial fibrillation pathophysiological outcome, the indicator threshold corresponding to a quantifiable physiological measure of a pathophysiology resulting from atrial fibrillation.

2. An automated method according to claim 1, further comprising:
   managing the atrial fibrillation diagnosis through administration of at least one of ventricular rate response control and normal sinus rhythm restoration.

3. An automated method according to claim 1, further comprising:
   periodically receiving a monitoring set for an individual patient, each recorded measure in the monitoring set having been recorded by at least one of a medical device adapted to be implanted in an individual patient and an external medical device proximal to the individual patient when the device measures are recorded; and
   storing the received monitoring set in the database as part of a patient care record for the individual patient.

4. An automated method according to claim 3, further comprising:
   defining a set of further indicator thresholds, each indicator threshold corresponding to a quantifiable physiological measure used to detect a pathophysiology indicative of diseases other than atrial fibrillation;
   comparing the patient status change to the such further indicator threshold corresponding to the same type of patient information as the at least one recorded measure and the at least one other recorded measure; and
   testing the patient status change against each such further indicator threshold corresponding to the same type of patient information as the recorded measures which were compared.

5. An automated method according to claim 1, further comprising:
   determining a change in patient status by comparing one or more recorded quality of life measure to one or more other corresponding recorded quality of life measure.

6. An automated method according to claim 1, further comprising:
   defining a set of stickiness indicators for the patient information, each stickiness indicator corresponding to a temporal limit related to a program of patient diagnosis or treatment;
   comparing a time span occurring between the patient status change for the recorded measure to the stickiness indicator relating to the same type of patient information as the recorded measure being compared; and
   determining a revised program of patient diagnosis or treatment responsive to the patient status change occurring subsequent to a time span exceeding the stickiness indicator.

7. An automated method according to claim 1, further comprising:
   retrieving the plurality of monitoring sets from one of a patient care record for an individual patient, a peer group, and a overall patient population.

8. An automated method according to claim 1, further comprising:
   retrieving a reference baseline comprising recorded measures with each recorded measure relating to patient information recorded during an initial time period and each recorded measure comprising either medical device measures or derived measures calculable therefrom; and
   obtaining at least one of the recorded measures and at least one other of the recorded measures from the retrieved reference baseline.

9. An automated method according to claim 1, wherein the indicator threshold relates to at least one of a finding of reduced exercise capacity, respiratory distress and palpitations/symptoms.

10. An automated method according to claim 9, wherein the indicator thresholds relating to the finding of reduced exercise capacity are selected from decreased cardiac output, decreased mixed venous oxygen score and decreased patient activity score.

11. An automated method according to claim 9, wherein the indicator thresholds relating to the finding of respiratory distress are selected from increased pulmonary artery diastolic pressure, increased respiratory rate and decreased transthoracic impedance.

12. A computer-readable storage medium containing code for an automated method for diagnosing and monitoring an outcome of atrial fibrillation, the code having instructions comprising:
   code for retrieving a plurality of monitoring sets from a database with each monitoring set comprising recorded measures relating to patient information recorded on a substantially continuous basis;
   code for diagnosing atrial fibrillation;
   code for determining a patient status change in response to the atrial fibrillation diagnosis for an absence, an onset, a progression, a regression, and a status quo of atrial fibrillation by comparing at least one of the recorded measures from each of the monitoring sets to at least one other of the recorded measures with both recorded measures relating to the same type of patient information; and code for testing the recorded measure comparison against an indicator threshold corresponding to the same type of patient information as the recorded measures which were compared to form the atrial fibrillation pathophysiological outcome, the indicator threshold corresponding to a quantifiable physiological measure of a pathophysiology resulting from atrial fibrillation.

13. A storage medium according to claim 12, the code further comprising:

code for diagnosing atrial fibrillation through administration of at least one of ventricular rate response control and normal sinus rhythm restoration.

14. A storage medium according to claim 12, the code further comprising:

code for periodically receiving a monitoring set for an individual patient, each recorded measure in the monitoring set having been recorded by at least one of a medical device adapted to be implanted in an individual patient and an external medical device proximal to the individual patient when the device measures are recorded; and code for storing the received monitoring set in the database as part of a patient care record for the individual patient.

15. A storage medium according to claim 14, further comprising:

code for defining a set of further indicator thresholds, each indicator threshold corresponding to a quantifiable physiological measure used to detect a pathophysiology indicative of diseases other than atrial fibrillation;

code for comparing the patient status change to the such further indicator threshold corresponding to the same type of patient information as the at least one recorded measure and the at least one other recorded measure; and code for testing the patient status change against each such further indicator threshold corresponding to the same type of patient information as the recorded measures which were compared.

16. A storage medium according to claim 12, the code further comprising:

code for determining a change in patient status by comparing one or more recorded quality of life measure to one or more other corresponding recorded quality of life measure.

17. A storage medium according to claim 12, the code further comprising:

code for defining a set of stickiness indicators for the patient measures, each stickiness indicator corresponding to a temporal limit related to a program of patient diagnosis or treatment;

code for comparing a time span occurring between the patient status change for the recorded measure to the stickiness indicator relating to the same type of patient information as the recorded measure being compared; and code for determining a revised program of patient diagnosis or treatment responsive to the patient status change occurring subsequent to a time span exceeding the stickiness indicator.

18. A storage medium according to claim 12, the code further comprising:

code for retrieving the plurality of monitoring sets from one of a patient care record for an individual patient, a peer group, and a overall patient population.

19. A storage medium according to claim 12, the code further comprising:

code for retrieving a reference baseline comprising recorded measures with each recorded measure relating to patient information recorded during an initial time period and each recorded measure comprising either medical device measures or derived measures calculable therefrom; and code for obtaining at least one of the recorded measures and the at least one other of the recorded measures from the retrieved reference baseline.

20. An automated collection and analysis patient care system for diagnosing and monitoring an of atrial fibrillation, comprising:

a database to store a plurality of monitoring sets, each monitoring set comprising recorded measures with each recorded measure relating to patient information and each recorded measure comprising either medical device measures or derived measures calculable therefrom, the medical device measures having been recorded on a substantially continuous basis;

a set of stored indicator thresholds, each indicator threshold corresponding to a quantifiable physiological measure of a pathophysiology resulting from atrial fibrillation and relating to the same type of patient information as at least one of the recorded measures; and a diagnostic module to diagnose atrial fibrillation;

an analysis module to determine a change in patient status status in response to the atrial fibrillation diagnosis for an absence, an onset, a progression, a regression, and a status quo of atrial fibrillation by comparing at least one of the recorded measures from each of the monitoring sets to at least one other of the recorded measures with both recorded measures relating to the same type of patient information; and a comparison module to compare the patient status change to at least one of the indicator thresholds corresponding to the same type of patient information as the recorded measures which were compared.

21. A system according to claim 20, the system further comprising:

at least one of a medical device adapted to be implanted in an individual patient and an external medical device proximal to the individual patient to record the device measures.

22. A system according to claim 20, wherein at least one of the monitoring sets comprises recorded measures relating to patient information solely for the individual patient, the system further comprising:

a database module to retrieve each monitoring set for the individual patient and obtaining at least one of the recorded measures from the at least one of the monitoring sets and at least one of the other recorded measures from the retrieved monitoring sets.

23. A system according to claim 20, wherein at least one of the monitoring sets comprises recorded measures relating to patient information for a peer group of patients to which the individual patient belongs, the system further comprising:

a database module to retrieve at least one of the monitoring sets for the individual patient, retrieving at least one other of the monitoring sets in the same patient peer group, and obtaining at least one of the recorded measures from the at least one monitoring set and at least one of the other recorded measures from the at least one other monitoring set.

24. A system according to claim 20, wherein at least one of the monitoring sets comprises recorded measures relating to patient information for the general population of patients, the system further comprising:
a database module to retrieve at least one of the monitoring sets for the individual patient, retrieving at least one other of the monitoring sets in the overall patient population, and obtaining at least one of the recorded measures from the at least one monitoring set and the-at least one of the other recorded measures from the at least one other monitoring set.

25. A system according to claim 20, the system further comprising:
the database further to store a reference baseline comprising recorded measures with each recorded measure relating to patient information recorded by the medical device adapted to be implanted during an initial time period and each recorded measure comprising either device measures recorded by the medical device adapted to be implanted or derived measures calculable therefrom; and
a database module to obtain at least one of the recorded measures and the-at least one other of the recorded measures from the reference baseline.

26. A system according to claim 25, wherein the reference baseline comprises recorded measures relating to patient information for one of the individual patients solely, a peer group of patients to which the individual patient belongs, and a general population of patients.

27. A system according to claim 20, the comparison module further comprising:
a module to grade comparisons between each the patient status change and the corresponding indicator threshold on a fixed scale by performing a degree of deviation from the indicator threshold; and
the comparison module to determine an overall patient status change by performing a summation over the comparisons.

28. A system according to claim 20, the comparison module further comprising:
a module to determine probabilistic weightings of comparisons between each the patient status change and the corresponding indicator threshold by performing a statistical deviation and trends via linear fits from the indicator threshold; and
the comparison module to determine an overall patient status change by performing a summation over each of the comparisons.

29. A system according to claim 20, wherein at least one monitoring set further comprises recorded quality of life and symptom measures, the diagnostic module further comprising:
a quality of life module to determine a change in the patient status by comparing at least one of the recorded quality of life measures in the database to at least one of the other corresponding recorded quality of life measures; and
the diagnostic module to incorporate the patient status change in quality of life into the atrial fibrillation finding to either refute or support the diagnosis.

30. A system according to claim 20, the system further comprising:
a set of stored further indicator thresholds, each of the further indicator thresholds corresponding to a quantifiable physiological measure used to detect a pathophysiology indicative of diseases other than atrial fibrillation; and
the diagnostic module to diagnose a finding of a disease other than atrial fibrillation by further comparing the patient status change to the such further indicator threshold corresponding to the same type of patient information as the at least the one recorded measure and the at least the one other recorded measure.

31. A system according to claim 20, the system further comprising:
a set of stickiness indicators, each of the stickiness indicators corresponding to a temporal limit related to a course of patient care; and
a feedback module to compare a time span between the patient status change for each recorded measure to the stickiness indicator corresponding to the same type of patient information as the recorded measure being compared.

32. A system according to claim 20, the system further comprising:
a feedback module to provide automated feedback to an individual patient when an atrial fibrillation is diagnosed.

33. A system according to claim 32, the system further comprising:
the feedback module to perform an interactive dialogue between the individual patient and the patient care system.

34. A method for diagnosing and monitoring an outcome of atrial fibrillation using an automated collection and analysis patient care system, the method comprising:
retrieving a plurality of monitoring sets from a database, each of the monitoring set comprising recorded measures with each recorded measure relating to patient information and each recorded measure comprising either medical device measures or derived measures calculable therefrom, the medical device measures having been recorded on a substantially continuous basis;
defining a set of indicator thresholds, each of the indicator threshold corresponding to a quantifiable physiological measure of a pathophysiology resulting from atrial fibrillation and relating to the same type of patient information as at least one of the recorded measures; and
diagnosing atrial fibrillation;
determining a change in patient status status in response to the atrial fibrillation diagnosis for an absence, an onset, a progression, a regression, and a status quo of atrial fibrillation by comparing at least one of the recorded measures from each of the monitoring sets to at least one other of the recorded measures with both recorded measures relating to the same type of patient information; and
comparing the patient status change to at least one of the indicator thresholds corresponding to the same type of patient information as the recorded measures which were compared.

35. A method according to claim 34, wherein further comprising:
recording the device measures by at least one of a medical device adapted to be implanted in an individual patient and an external medical device proximal to the individual patient.

36. A method according to claim 35, wherein at least one of the monitoring sets comprises recorded measures relating to patient information solely for the individual patient, the method further comprising:

retrieving each monitoring set for the individual patient; and obtaining at least one of the recorded measures from the at least one monitoring set and at least one of the other recorded measures from the retrieved monitoring sets.

37. A method according to claim 34, wherein at least one of the monitoring sets comprises recorded measures relating to patient information for a peer group of patients to which the individual patient belongs, the method further comprising:

retrieving at least one of the monitoring sets for the individual patient;

retrieving at least one other of the monitoring sets in the same patient peer group; and obtaining at least one of the recorded measures from the at least one monitoring set and at least one of the other recorded measures from the at least one other monitoring set.

38. A method according to claim 34, wherein at least one of the monitoring sets comprises recorded measures relating to patient information for the general population of patients, the method further comprising:

retrieving at least one of the monitoring sets for the individual patient;

retrieving at least one other of the monitoring sets in the overall patient population; and obtaining at least one of the recorded measures from the at least one monitoring set and at least one of the other recorded measures from the at least one other monitoring set.

39. A method according to claim 34, further comprising:

retrieving a reference baseline, the reference baseline comprises recorded measures with each recorded measure relating to patient information recorded by the medical device adapted to be implanted during an initial time period and each recorded measure comprising either device measures recorded by the medical device adapted to be implanted or derived measures calculable therefrom; and obtaining at least one of the recorded measures from the at least one monitoring set and at least one of the other recorded measures from the reference baseline.

40. A method according to claim 39, wherein the reference baseline comprises recorded measures relating to patient information for one of the individual patients solely, a peer group of patients to which the individual patient belongs, and a general population of patients.

41. A method according to claim 34, wherein the operation of comparing the patient status change further comprises:

grading the comparisons between the patient status change and corresponding indicator threshold on a fixed scale by performing a degree of deviation from the indicator threshold; and determining an overall patient status change by performing a summation over the comparisons.

42. A method according to claim 34, wherein the operation of comparing the patient status change further comprises:

determining probabilistic weightings of comparisons between the patient status change and corresponding indicator threshold by performing a statistical deviation and trends via linear fits from the indicator threshold; and determining an overall patient status change by performing a summation over each of the comparisons.

43. A method according to claim 34, wherein at least one of the monitoring sets further comprises recorded quality of life and symptom measures, the operation of diagnosing an atrial fibrillation finding further comprising:

determining a change in patient status by comparing at least one recorded quality of life measure to at least one other corresponding recorded quality of life measure; and incorporating the patient status change in quality of life into the atrial fibrillation finding to either refute or support the diagnosis.

44. A method according to claim 34, further comprising:

defining a set of further indicator thresholds, each further indicator threshold corresponding to a quantifiable physiological measure used to detect a pathophysiology indicative of diseases other than atrial fibrillation; and diagnosing a finding of the disease other than atrial fibrillation, comprising comparing the patient status change to each such further indicator threshold corresponding to the same type of patient information as the at least one recorded measure and the at least one other recorded measure.

45. A method according to claim 34, further comprising:

defining a set of stickiness indicators, each of the stickiness indicators corresponding to a temporal limit related to a course of patient care; and comparing a time span between the patient status change for each recorded measure to the stickiness indicator corresponding to the same type of patient information as the recorded measure being compared.

46. A method according to claim 34, further comprising:

providing automated feedback to an individual patient when atrial fibrillation is diagnosed.

47. A method according to claim 46, further comprising:

performing an interactive dialogue between the individual patient and the patient care system.

48. A computer-readable storage medium holding code for diagnosing and monitoring an outcome of atrial fibrillation using an automated collection and analysis patient care system, the code having instructions comprising:

code for retrieving a plurality of monitoring sets from a database, each monitoring set comprising recorded measures with each recorded measure relating to patient information and each recorded measure comprising either medical device measures or derived measures calculable therefrom, the medical device measures having been recorded on a substantially continuous basis;

code for defining a set of indicator thresholds, each indicator threshold corresponding to a quantifiable physiological measure of a pathophysiology resulting from atrial fibrillation and relating to the same type of patient information as at least one of the recorded measures; and code for diagnosing atrial fibrillation;

code for determining a change in patient status status in response to the atrial fibrillation diagnosis for an absence, an onset, a progression, a regression, and a status quo of atrial fibrillation by comparing at least one of the recorded measures from each of the monitoring sets to at least one other of the recorded measures with both recorded measures relating to the same type of patient information; and code for comparing the patient status change to at least one of the indicator thresholds corresponding to the same type of patient information as the recorded measures which were compared.

49. A storage medium according to claim 48, wherein at least one of the monitoring sets comprises recorded measures relating to patient information solely for the individual patient, the code further comprising:

code for retrieving each monitoring set from for the individual patient; and code for obtaining at least one of the recorded measures from the at least one monitoring set and at least one of the other recorded measures from the retrieved monitoring sets.

50. A storage medium according to claim 48, wherein at least one of the monitoring sets comprises recorded measures relating to patient information for a peer group of patients to which the individual patient belongs, the code further comprising:

code for retrieving at least one of the monitoring sets for the individual patient;

code for retrieving at least one other of the monitoring sets in the same patient peer group; and code for obtaining at least one of the recorded measures from the at least one monitoring set and at least one of the other recorded measures from the at least one other monitoring set.

51. A storage medium according to claim 48, wherein at least one of the monitoring sets comprises recorded measures relating to patient information for the general population of patients, the code further comprising:

code for at least one of the monitoring sets for the individual patient;

code for retrieving at least one other of the monitoring sets in the overall patient population; and code for obtaining at least one of the recorded measures from the at least one monitoring set and at least one of the other recorded measures from the at least one other monitoring set.

52. A storage medium according to claim 48, code further comprising:

code for retrieving a reference baseline, the reference baseline comprises comprising recorded measures with each recorded measure relating to patient information recorded by the medical device adapted to be implanted during an initial time period and each recorded measure comprising either device measures recorded by the medical device adapted to be implanted or derived measures calculable therefrom; and code for obtaining at least one of the recorded measures from the at least one monitoring set and at least one of the other recorded measures from the reference baseline.

53. A storage medium according to claim 48, wherein the operation of comparing the patient status change, the code further comprises:

code for grading the comparisons between the patient status change and corresponding indicator threshold on a fixed scale by performing a degree of deviation from the indicator threshold; and code for determining an overall patient status change by performing a summation over the comparisons.

54. A storage medium according to claim 37, wherein the operation of comparing the patient status change, the code further comprises:

code for determining probabilistic weightings of comparisons between the patient status change and corresponding indicator threshold by performing a statistical deviation and trends via linear fits from the indicator threshold; and code for determining an overall patient status change by performing a summation over the comparisons.

55. A storage medium according to claim 48, wherein at least one of the monitoring sets further comprises quality of life and symptom measures recorded by an individual patient, the operation of diagnosing an atrial fibrillation finding, the code further comprising:

code for determining a change in patient status by comparing at least one recorded quality of life measure to at least one other corresponding recorded quality of life measure; and code for incorporating the patient status change in quality of life into the atrial fibrillation finding to either refute or support the diagnosis.

56. A storage medium according to claim 48, the code further comprising:

code for defining a set of further indicator thresholds, each further indicator threshold corresponding to a quantifiable physiological measure used to detect a pathophysiology indicative of diseases other than atrial fibrillation; and code for diagnosing a finding of the disease other than atrial fibrillation, comprising comparing the patient status change to each such further indicator threshold corresponding to the same type of patient information as the at least one recorded measure and the at least one other recorded measure.

57. A storage medium according to claim 48, the code further comprising:

code for defining a set of stickiness indicators, each of the stickiness indicators corresponding to a temporal limit related to a course of patient care; and code for comparing a time span between the patient status change for each recorded measure to the stickiness indicator corresponding to the same type of patient information as the recorded measure being compared.

58. A storage medium according to claim 48, the code further comprising:

code for providing automated feedback to the an individual patient when an atrial fibrillation is diagnosed.

59. A storage medium according to claim 48, the code further comprising:

code for performing an interactive dialogue between the individual patient and the patient care system.

60. An automated patient care system for diagnosing and monitoring an outcome of atrial fibrillation the system comprising:

a diagnostic module to diagnose atrial fibrillation;

a database to store recorded measures organized into a monitoring set for an individual patient with each recorded measure having been recorded on a substantially continuous basis and relating to at least one of monitoring reduced exercise capacity and respiratory distress;

a database module to periodically retreive a plurality of the monitoring sets from the database; and an evaluation module to evaluate at least one of atrial fibrillation onset, progression, regression, and status quo;

a comparison module to determine a patient status change in response to an atrial fibrillation diagnosis by comparing at least of the one recorded measures from each of the monitoring sets to at least one other of the recorded measures with both recorded measures relating to the same type of patient information; and an analysis module to test the patient status change against an indicator threshold corresponding to the same type of patient information as the recorded measures which were compared, the indicator threshold corresponding to a quantifiable physiological measure of a pathophysiology indicative of reduced exercise capacity and respiratory distress.

61. A method for diagnosing and monitoring the an outcome of atrial fibrillation in an automated patient care system the method comprising:

diagnosing atrial fibrillation;

storing recorded measures organized into a monitoring set for an individual patient into a database with each recorded measure having been recorded on a substantially continuous basis and relating to at least one of monitoring reduced exercise capacity and respiratory distress;

periodically retrieving a plurality of the monitoring sets from the database;

evaluating at least one of atrial fibrillation onset, progression, regression, and status quo;

determining a patient status change in response to an atrial fibrillation by comparing at least of the one recorded measures from each of the monitoring sets to at least one other of the recorded measures with both recorded measures relating to the same type of patient information; and testing the patient status change against an indicator threshold corresponding to the same type of patient information as the recorded measures which were compared, the indicator threshold corresponding to a quantifiable physiological measure of a pathophysiology indicative of reduced exercise capacity and respiratory distress.

62. A computer-readable storage medium holding code for diagnosing and monitoring an outcome of atrial fibrillation in an automated patient care system, the code having instructions comprising:

code for diagnosing atrial fibrillation;

code for storing recorded measures organized into a monitoring set for an individual patient into a database with each recorded measure having been recorded on a substantially continuous basis and relating to at least one of monitoring reduced exercise capacity and respiratory distress;

code for periodically retrieving a plurality of the monitoring sets from the database;

code for evaluating at least one of atrial fibrillation onset, progression, regression, and status quo;

code for determining a patient status change in response to an atrial fibrillation diagnosis by comparing at least of the one recorded measures from each of the monitoring sets to at least one other of the recorded measures with both recorded measures relating to the same type of patient information; and code for testing the patient status change against an indicator threshold corresponding to the same type of patient information as the recorded measures which were compared, the indicator threshold corresponding to a quantifiable physiological measure of a pathophysiology indicative of reduced exercise capacity and respiratory distress.

* * * * *

UNITED STATES PATENT AND TRADEMARK OFFICE
CERTIFICATE OF CORRECTION

PATENT NO. : 6,704,595 B2
DATED : March 9, 2004
INVENTOR(S) : Bardy, Gust H.

It is certified that error appears in the above-identified patent and that said Letters Patent is hereby corrected as shown below:

Column 30,
Line 15, "and the-at least one other of the recorded measures" should read -- and at least one other of the recorded measures --.

Column 31,
Line 16, "measures from the at least one monitoring set and the-at" should read -- measures from at least one monitoring set and at --;
Line 29, "measures and the-at least one other of the recorded" should read -- measures and at least one other of the recorded --.

Column 32,
Line 27, "individual patient when an atrial fibrillation is diag" should read -- individual patient when atrial fibrillation is diag --;
Line 64, "A method according to claim 34, wherein further" should read -- A method according to claim 34, further --.

Column 35,
Line 46, "A storage medium according to claim 48, code further" should read -- A storage medium according to claim 48, the code further --.

Column 36,
Line 49, "code for providing automated feedback to the an indi-" should read -- code for providing automated feedback to an indi --;
Line 50, "vidual patient when an atrial fibrillation is diagnosed." should read -- vidual patient when atrial fibrillation is diagnosed --;
Line 66, "a database module to periodically retreive a plurality of" should read -- a database module to periodically retrieve a plurality of --.

UNITED STATES PATENT AND TRADEMARK OFFICE
CERTIFICATE OF CORRECTION

PATENT NO. : 6,704,595 B2
DATED : March 9, 2004
INVENTOR(S) : Bardy, Gust H.

It is certified that error appears in the above-identified patent and that said Letters Patent is hereby corrected as shown below:

Column 37,
Line 17, "A method for diagnosing and monitoring the an" should read
-- A method for diagnosing and monitoring an --.

Signed and Sealed this

Twenty-eighth Day of June, 2005

JON W. DUDAS
*Director of the United States Patent and Trademark Office*